US012679845B2

(12) United States Patent
Su et al.

(10) Patent No.: US 12,679,845 B2
(45) Date of Patent: Jul. 14, 2026

(54) CRYSTAL FORM OF TRIAZOLOPYRIDINE-SUBSTITUTED INDAZOLE COMPOUND AND PREPARATION METHOD THEREFOR

(71) Applicant: SHENZHEN OPTIMUM BIOLOGICAL TECHNOLOGY CO., LTD, Shenzhen (CN)

(72) Inventors: Sheng Su, Shanghai (CN); Yunfu Luo, Shanghai (CN); Guoli Zhang, Shanghai (CN)

(73) Assignee: SHENZHEN OPTIMUM BIOLOGICAL TECHNOLOGY CO., LTD., Shenzhen (CN)

( * ) Notice: Subject to any disclaimer, the term of this patent is extended or adjusted under 35 U.S.C. 154(b) by 293 days.

(21) Appl. No.: 18/574,378

(22) PCT Filed: Jun. 23, 2022

(86) PCT No.: PCT/CN2022/100911
§ 371 (c)(1),
(2) Date: Feb. 1, 2024

(87) PCT Pub. No.: WO2023/274040
PCT Pub. Date: Jan. 5, 2023

(65) Prior Publication Data

US 2024/0246985 A1 Jul. 25, 2024

(30) Foreign Application Priority Data

Jun. 28, 2021 (CN) ......................... 202110722010.6

(51) Int. Cl.
*A61K 31/437* (2006.01)
*C07D 487/04* (2006.01)

(52) U.S. Cl.
CPC .......... *C07D 487/04* (2013.01); *A61K 31/437* (2013.01)

(58) Field of Classification Search
CPC ............................ C07D 487/04; A61K 31/437
See application file for complete search history.

(56) References Cited

FOREIGN PATENT DOCUMENTS

| | | | | |
|---|---|---|---|---|
| CN | 101611015 A | | 12/2009 | |
| CN | 102112449 A | | 6/2011 | |
| CN | 109415348 A | | 3/2019 | |
| WO | WO-2021136429 A1 | * | 7/2021 | ........... C07D 487/04 |

OTHER PUBLICATIONS

Ripa et al., Discovery of a Novel Oral Glucocorticoid Receptor Modulator (AZD9567) with Improved Side Effect Profile, Feb. 9, 2018, Journal of Medicinal Chemistry, vol. 61, pp. 1785-1799. (Year: 2018).*
Jun. 10, 2025 Extended European Search Report issued in European Patent Application No. 22831854.9.
Sep. 21, 2022 International Search Report issued in International Patent Application No. PCT/CN2022/100911.
Sep. 21, 2022 Written Opinion of the International Searching Authority issued in International Patent Application No. PCT/CN2022/100911.
Ripa, Lena et al., "Discovery of a Novel Oral Glucocorticoid Receptor Modulator (AZD9567) with Improved Side Effect Profile." Journal of Medicinal Chemistry, vol. 61(5), pp. 1785-1799, 2018.
Hemmerling Martin et al., "Selective Non-steroidal Glucocorticoid Receptor Modulators for the Inhaled Treatment of Pulmonary Diseases," Journal of Medicinal Chemistry, vol. 60(20), pp. 8591-8605, 2017.

* cited by examiner

*Primary Examiner* — Ali Soroush
(74) *Attorney, Agent, or Firm* — Harness, Dickey & Pierce, P.L.C.

(57) ABSTRACT

Provided are a crystal form of a triazolopyridine-substituted indazole compound and a preparation method therefor; and specifically disclosed are a crystal form of a compound as represented by formula (I) and a preparation method therefor.

(I)

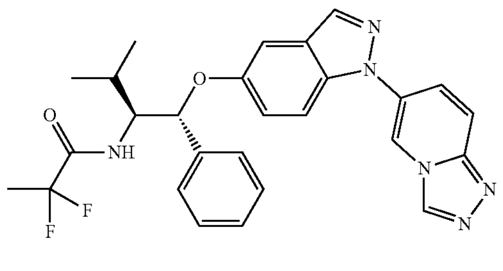

19 Claims, 5 Drawing Sheets

CRYSTAL FORM OF TRIAZOLOPYRIDINE-SUBSTITUTED INDAZOLE COMPOUND AND PREPARATION METHOD THEREFOR

CROSS-REFERENCE TO RELATED APPLICATIONS

The present application is a U.S. National Phase Application under 35 U.S.C. 371 of International Application No. PCT/CN2022/100911, filed on Jun. 23, 2022, which claims priority to Chinese Patent Application No. 202110722010.6, filed on Jun. 28, 2021. The entire disclosure of the aforementioned Chinese patent application is incorporated herein by reference.

TECHNICAL FIELD

The present disclosure relates to a crystal form of a triazolopyridine-substituted indazole compound and a preparation method therefor, specifically to a crystal form of a compound of formula (I) and a preparation method therefor.

BACKGROUND

Rheumatoid arthritis (RA) is a chronic inflammatory and "systemic" autoimmune disease. The articular manifestations of early rheumatoid arthritis are often difficult to distinguish from other types of inflammatory arthritis. Rheumatoid arthritis has more characteristic signs, such as articular erosions, rheumatoid nodules, and other extra-articular manifestations. Rheumatoid arthritis affects more women than men (3:1), and the age of onset is between 30 and 55 years.

The pathogenesis of rheumatoid arthritis is very complex, mainly due to the fact that autoantigens are presented by major histocompatibility complex II (MHC-II)-positive antigen-presenting cells (APCs) to activated $CD4^+$ T cells, which initiates a specific immune response; at the same time, the migration of activated T cells and macrophages to the synovium leads to an increase in the secretion of a variety of inflammatory cytokines, such as TNFα, IL-1, and IL-6, and infiltration of synovial joints, resulting in the corresponding symptoms of arthritis.

Glucocorticoids (GCs) have been widely used for decades to treat inflammatory and immune diseases, including rheumatoid arthritis, asthma, chronic obstructive pulmonary disease (COPD), osteoarthritis, rheumatic fever, allergic rhinitis, systemic lupus erythematosus, Crohn's disease, inflammatory bowel disease, and ulcerative colitis.

Glucocorticoids (GCs) bind to glucocorticoid receptors (GRs) and enter the cell nucleus to affect gene transcription (activation and repression) and reduce the production of inflammatory factors. The glucocorticoid receptor is a member of the conserved nuclear receptor superfamily as a nuclear transcription factor. GC is widely present in various tissue cells of the body, and almost all cells are its target cells. GC plays an important regulatory role in the development, growth, metabolism, and immune function of the body. GC usually has serious and irreversible side effects, such as osteoporosis, hyperglycemia, diabetes, hypertension, muscular dystrophy, and Cushing's syndrome, which severely limits the use of GC in chronic diseases.

Examples of GR ligands, called selective glucocorticoid receptor modulators (SGRMs), that can selectively induce transcriptional repression without significant transcriptional activation, and can reduce the risk of systemic side effects while maintaining anti-inflammatory activity, have been found. Selective glucocorticoid receptor modulators (SGRMs) differ from GCs in that they can trigger complete transcriptional repression and only trigger partial transcriptional activation when binding to GR, thereby controlling related side effects while maintaining anti-inflammatory activity.

CONTENT OF THE PRESENT INVENTION

The present disclosure provides a crystal form Q of a compound of formula (I), which has an X-ray powder diffraction pattern comprising characteristic diffraction peaks at the following 2θ angles: 10.301±0.200°, 17.459±0.200°, and 19.141±0.200°, (I)

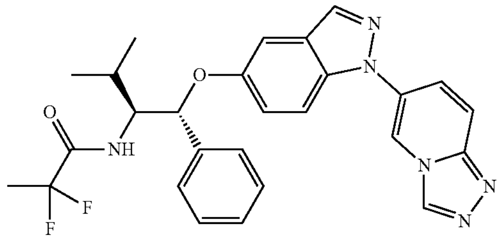

8.060±0.200°, 10.301±0.200°, 12.779±0.200°, 16.860-0.200°, 17.459±0.200°, 17.870±0.200°, 18.639±0.200°, 19.141±0.200°, 20.701±0.200°, 21.701±0.200°, 22.579±0.200°, and 24.400±0.200°.

In some embodiments of the present disclosure, the X-ray powder diffraction pattern of the crystal form Q comprises characteristic diffraction peaks at the following 2θ angles: 3.861±0.200°, 8.060±0.200°, 9.621±0.200°, 10.301±0.200°, 11.500±0.200°, 12.779±0.200°, 16.860±0.200°, 17.459±0.200°, 17.870±0.200°, 18.639±0.200°, 19.141±0.200°, 20.701±0.200°, 21.701±0.200°, 22.579±0.200°, 24.400±0.200°, and 24.939±0.200°.

In some embodiments of the present disclosure, the X-ray powder diffraction pattern of the crystal form Q comprises characteristic diffraction peaks at the following 2θ angles: 3.322°, 3.861°, 4.899°, 6.421°, 7.440°, 8.060°, 8.722°, 9.621°, 10.301°, 11.500°, 12.779°, 13.197°, 14.321°, 15.041°, 15.859°, 16.860°, 17.459°, 17.870°, 18.639°, 19.141°, 20.701°, 21.701°, 22.579°, 24.400°, 24.939°, 25.700°, 26.602°, and 27.201°.

The present disclosure provides the crystal form Q of the compound of formula (I), wherein the X-ray powder diffraction pattern of the crystal form Q comprises characteristic diffraction peaks at the following 2θ angles: 10.301±0.200°, 17.459±0.200°, and 19.141±0.200°, and can further comprise characteristic diffraction peaks at the following 20 angles: 24.400±0.200°, and/or 16.860±0.200°, and/or 12.779±0.200°, and/or 21.701±0.200°, and/or 20.701±0.200°, and/or 8.060±0.200°, and/or 22.579±0.200°, and/or 17.8700.200°, and/or 18.639±0.200°, and/or 3.861±0.200°, and/or 24.939±0.200°, and/or 9.621±0.200°, and/or 11.500±0.200°, and/or 6.4210.200°, and/or 4.899±0.200°, and/or 26.602±0.200°, and/or 3.322±0.200°, and/or 7.440±0.200°, and/or 13.197±0.200°, and/or 25.700±0.200°, and/or 14.321±0.200°, and/or 8.722±0.200°, and/or 15.859±0.200°, and/or 27.201±0.200°, and/or 15.041±0.200°.

In some embodiments of the present disclosure, the crystal form Q of the compound has an XRPD pattern as shown in FIG. 1.

In some embodiments of the present disclosure, the analysis data of the XRPD pattern of the crystal form Q are as shown in Table 1.

TABLE 1

Analysis data of XRPD pattern of crystal form Q of compound of formula (I)

| No. | 2θ angle (°) | d-Spacing (Å) | Peak height | Peak height (%) |
|---|---|---|---|---|
| 1 | 3.322 | 26.5788 | 269 | 17.1 |
| 2 | 3.861 | 22.8635 | 376 | 23.9 |
| 3 | 4.899 | 18.0239 | 280 | 17.8 |
| 4 | 6.421 | 13.7540 | 286 | 18.2 |
| 5 | 7.440 | 11.8722 | 258 | 16.4 |
| 6 | 8.060 | 10.9612 | 412 | 26.2 |
| 7 | 8.722 | 10.1304 | 203 | 12.9 |
| 8 | 9.621 | 9.1858 | 339 | 21.6 |
| 9 | 10.301 | 8.5807 | 1572 | 100 |
| 10 | 11.500 | 7.6882 | 315 | 20.1 |
| 11 | 12.779 | 6.9216 | 494 | 31.4 |
| 12 | 13.197 | 6.7034 | 246 | 15.7 |
| 13 | 14.321 | 6.1795 | 215 | 13.7 |
| 14 | 15.041 | 5.8855 | 162 | 10.3 |
| 15 | 15.859 | 5.5839 | 183 | 11.7 |
| 16 | 16.860 | 5.2544 | 604 | 38.4 |
| 17 | 17.459 | 5.0755 | 762 | 48.5 |
| 18 | 17.870 | 4.9595 | 398 | 25.3 |
| 19 | 18.639 | 4.7567 | 378 | 24.1 |
| 20 | 19.141 | 4.6330 | 690 | 43.9 |
| 21 | 20.701 | 4.2874 | 420 | 26.7 |
| 22 | 21.701 | 4.0919 | 445 | 28.3 |
| 23 | 22.579 | 3.9347 | 404 | 25.7 |
| 24 | 24.400 | 3.6451 | 664 | 42.2 |
| 25 | 24.939 | 3.5675 | 369 | 23.5 |
| 26 | 25.700 | 3.4635 | 241 | 15.3 |
| 27 | 26.602 | 3.3482 | 277 | 17.6 |
| 28 | 27.201 | 3.2758 | 173 | 11.0 |

In some embodiments of the present disclosure, the crystal form Q has a differential scanning calorimetry (DSC) curve comprising endothermic peaks with an onset at 181.4° C.±5° C.

In some embodiments of the present disclosure, the crystal form Q has a DSC pattern as shown in FIG. 2.

In some embodiments of the present disclosure, the crystal form Q has a thermogravimetric analysis (TGA) curve with a weight loss of 1.47% at 150° C.±3° C.

In some embodiments of the present disclosure, the crystal form Q has a TGA pattern as shown in FIG. 3.

The present disclosure also provides a preparation method for the crystal form Q of the compound of formula (I), comprising:

(a) adding the compound of formula (I) to a solvent to make a suspension;

(b) stirring at 50 to 55° C. for 96 to 120 hours; and (c) vacuum drying for 8 to 16 hours after filtration;

wherein the solvent is methyl isobutyl ketone and n-heptane with a volume ratio of 1:6.

The present disclosure also provides a crystal form S of the compound of formula (I), which has an X-ray powder diffraction pattern comprising characteristic diffraction peaks at the following 2θ angles: 13.019±0.200°, 19.579±0.200°, and 20.262±0.200°, (I)

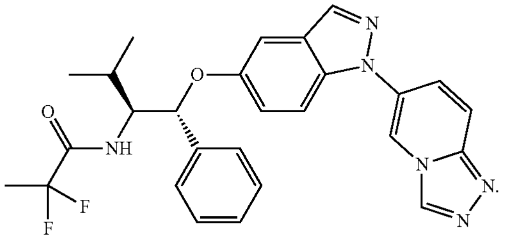

In some embodiments of the present disclosure, the X-ray powder diffraction pattern of the crystal form S comprises characteristic diffraction peaks at the following 2θ angles: 11.999±0.200°, 13.019±0.200°, 14.961±0.200°, 18.182±0.200°, 19.579±0.200°, 20.262±0.200°, 22.939±0.200°, and 24.021±0.200°.

In some embodiments of the present disclosure, the X-ray powder diffraction pattern of the crystal form S comprises characteristic diffraction peaks at the following 2θ angles: 3.201±0.200°, 11.463±0.200°, 11.999±0.200°, 13.019±0.200°, 14.523±0.200°, 14.961±0.200°, 18.182±0.200°, 19.579±0.200°, 20.262±0.200°, 22.939±0.200°, 24.021±0.200°, and 25.738±0.200°.

In some embodiments of the present disclosure, the X-ray powder diffraction pattern of the crystal form S comprises characteristic diffraction peaks at the following 2θ angles: 11.463±0.200°, 11.999±0.200°, 13.019±0.200°, 14.523±0.200°, 14.961±0.200°, 18.182±0.200°, 19.579±0.200°, 20.262±0.200°, 22.939±0.200°, 24.021±0.200°, and 25.738±0.200°.

In some embodiments of the present disclosure, the crystal form S has an XRPD pattern as shown in FIG. 5.

In some embodiments of the present disclosure, the analysis data of the XRPD pattern of the crystal form S are as shown in Table 2:

TABLE 2

Analysis data of XRPD pattern of crystal form S of compound of formula (I)

| No. | 2θ angle (°) | d-Spacing (Å) | Peak height | Peak height (%) |
|---|---|---|---|---|
| 1 | 3.201 | 27.5829 | 205 | 19.1 |
| 2 | 4.481 | 19.7024 | 146 | 13.6 |
| 3 | 10.262 | 8.6134 | 152 | 14.2 |
| 4 | 10.874 | 8.1293 | 78 | 7.3 |
| 5 | 11.463 | 7.7135 | 163 | 15.3 |
| 6 | 11.999 | 7.3697 | 469 | 43.7 |
| 7 | 13.019 | 6.7947 | 1071 | 100 |
| 8 | 13.740 | 6.4396 | 55 | 5.2 |
| 9 | 14.523 | 6.0942 | 172 | 16.0 |
| 10 | 14.961 | 5.9169 | 208 | 19.5 |
| 11 | 15.818 | 5.5979 | 66 | 6.2 |
| 12 | 18.182 | 4.8753 | 349 | 32.6 |
| 13 | 18.541 | 4.7816 | 201 | 18.8 |
| 14 | 18.879 | 4.6967 | 144 | 13.5 |
| 15 | 19.579 | 4.5304 | 547 | 51.1 |
| 16 | 20.262 | 4.3791 | 575 | 53.7 |
| 17 | 21.120 | 4.2031 | 80 | 7.5 |
| 18 | 21.679 | 4.0961 | 48 | 4.5 |
| 19 | 22.378 | 3.9696 | 110 | 10.2 |
| 20 | 22.939 | 3.8738 | 295 | 27.5 |
| 21 | 24.021 | 3.7017 | 454 | 42.4 |
| 22 | 24.502 | 3.6302 | 148 | 13.8 |
| 23 | 25.738 | 3.4585 | 177 | 16.5 |
| 24 | 27.103 | 3.2874 | 38 | 3.5 |
| 25 | 28.680 | 3.1101 | 46 | 4.2 |

TABLE 2-continued

Analysis data of XRPD pattern of crystal form S of compound of formula (I)

| No. | 2θ angle (°) | d-Spacing (Å) | Peak height | Peak height (%) |
|---|---|---|---|---|
| 26 | 29.200 | 3.0559 | 56 | 5.2 |
| 27 | 30.841 | 2.8970 | 52 | 4.9 |
| 28 | 31.878 | 2.8050 | 32 | 3.0 |
| 29 | 33.219 | 2.6948 | 38 | 3.6 |
| 30 | 34.481 | 2.5990 | 29 | 2.7 |
| 31 | 35.623 | 2.5182 | 52 | 4.8 |

In some embodiments of the present disclosure, the crystal form S has a differential scanning calorimetry (DSC) curve comprising an endothermic peak at 114.9° C.±3° C.

In some embodiments of the present disclosure, the crystal form S has a DSC pattern as shown in FIG. 6.

In some embodiments of the present disclosure, the crystal form S has a thermogravimetric analysis (TGA) curve with a weight loss of 0.99% at 90.0° C.±3° C. and a weight loss of 2.54% at 120.0° C.±3° C.

In some embodiments of the present disclosure, the crystal form S has a TGA pattern as shown in FIG. 7.

The present disclosure also provides a preparation method for the crystal form S of the compound of formula (I), comprising:

(a) adding the compound of formula (I) to a solvent to make a suspension;

(b) stirring the suspension at 80 to 85° C. for 2 to 3 hours to gradually clarify;

(c) slowly cooling to 20 to 25° C. to precipitate a white solid; and (d) vacuum drying for 8 to 16 hours after filtration;

wherein the solvent is selected from ethyl acetate.

The present disclosure also provides a use of the crystal form Q and crystal form S or the crystal form Q and crystal form S prepared according to the methods in the manufacture of a medicament for the treatment of rheumatoid arthritis.

Technical Effect

The compound of the present disclosure can bind to glucocorticoid receptors, possesses good gene transcriptional repression activity and moderate gene transcriptional activation activity, improves cellular anti-inflammatory activity while reducing side effects such as hyperglycemia and osteoporosis, and has favorable PK properties and oral absorption rate, which can be used for the treatment of rheumatoid arthritis. The crystal form of the compound of the present disclosure is stable, has good hygroscopicity, and is less susceptible to light and heat.

Definition and Description

Unless otherwise specified, the following terms and phrases when used herein have the following meanings. A specific phrase or term should not be considered indefinite or unclear in the absence of a particular definition, but should be understood in the ordinary sense. When a trading name appears herein, it is intended to refer to its corresponding commodity or active ingredient thereof.

The intermediate compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include, but are not limited to, the examples of the present disclosure.

The chemical reactions of the specific embodiments of the present disclosure are completed in a suitable solvent, and the solvent must be appropriate for the chemical changes of the present disclosure and the required reagents and materials thereof. In order to obtain the compounds of the present disclosure, it is sometimes necessary for those skilled in the art to modify or select the synthetic steps or reaction processes on the basis of the existing embodiments.

The structure of the compounds of the present disclosure can be confirmed by conventional methods known to those skilled in the art, and if the present disclosure involves an absolute configuration of a compound, then the absolute configuration can be confirmed by means of conventional techniques in the art. For example, in the case of single crystal X-ray diffraction (SXRD), diffraction intensity data are collected from the cultured single crystal using a Bruker D8 venture diffractometer with CuKα radiation as the light source and scanning mode: φ/ω scan, and after collecting the relevant data, the crystal structure is further analyzed by direct method (Shelxs97), so that the absolute configuration can be confirmed.

Unless otherwise specified, in the DSC pattern, the upward peak is exothermic.

The present disclosure is described in detail by the examples below, but these examples do not imply any restrictions on the present disclosure.

All solvents used in the present disclosure are commercially available and can be used without further purification.

The following abbreviations are used in the present disclosure: PhMgBr represents phenylmagnesium bromide; $(i\text{-PrO})_3Al$ represents aluminum isopropoxide; $T_3P$ represents propylphosphonic anhydride; $Cs_2CO_3$ represents cesium carbonate; $K_2CO_3$ represents potassium carbonate; i-PrOH represents isopropanol; MeCN represents acetonitrile; DCM represents dichloromethane; THF represents tetrahydrofuran; EtOAc represents ethyl acetate; MeOH represents methanol; 1,4-dioxane represents 1,4-dioxane; MIBK represents methyl isobutyl ketone; n-Heptane represents n-heptane.

The compounds of the present disclosure are named according to the conventional naming principles in the art or by ChemDraw® software, and the commercially available compounds use the supplier catalog names.

X-Ray Powder Diffraction (X-Ray Powder Diffractometer, XRPD) Method of the Present Disclosure Instrument model: DX-2700BH X-ray diffractometer Test method: Approximately 10 to 20 mg of sample is used for XRPD detection.

The detailed XRPD parameters are as follows:

Light tube: Cu, kα, (2=1.54056 Å).

Light tube voltage: 40 kV, light tube current: 40 mA

Divergence slit: 1 mm

Detector slit: 0.3 mm

Anti-scatter slit: 1 mm

Scan range: 3 to 40 deg

Step size: 0.02 deg

Scan time: 0.5 s

Differential Scanning Calorimetry (Differential Scanning Calorimeter, DSC) Method of the Present Disclosure Instrument model: TA Instruments Discovery DSC 2500 differential scanning calorimeter The sample (1 to 5 mg) is placed in an alumina crucible with a cover lid and tested under the protection of 50 mL/min dry nitrogen, and the method is: heating from 25° C. to the set test temperature at a rate of 10° C./min.

Thermogravimetric Analysis (Thermal Gravimetric Analyzer, TGA) Method of the Present Disclosure Instrument model: TA Discovery TGA 5500 thermal gravimetric analyzer Test method: The sample (2 to 5 mg) is placed in a platinum pot and tested under the protection of 25 mL/min dry nitrogen, and the method is: heating from room temperature to 350° C. at a rate of 10° C./min.

Dynamic Vapor Sorption (DVS) Method of the Present Disclosure

Instrument model: SMS (Surface Measurement Systems) dynamic vapor sorption analyzer Test conditions: The sample (10 to 15 mg) is taken and placed in a DVS sample dish for testing.

The detailed DVS parameters are as follows:

Temperature: 25° C.

Equilibrium: dm/dt=0.002%/min (minimum: 10 min, maximum: 180 min)

Drying: drying for 120 min under 0% RH

RH (%) Test Gradient:

10% (0% RH to 90% RH, 90% RH to 0% RH)

5% (90% RH to 95% RH, 95% RH to 90% RH) RH (%)

RH (%) test gradient range: 0% to 95%

The evaluation and classification of hygroscopicity are shown in Table 3:

TABLE 3

Evaluation and classification of hygroscopicity

| Classification of hygroscopicity | ΔW % |
|---|---|
| Deliquescence | Absorption of sufficient water to form a liquid |
| Highly hygroscopic | ΔW % ≥ 15% |
| Hygroscopic | 15% > ΔW % ≥ 2% |
| Slightly hygroscopic | 2% > ΔW % ≥ 0.2% |
| Non-hygroscopic or virtually non-hygroscopic | ΔW % < 0.2% |

Note:
ΔW % represents the hygroscopic weight gain of the test sample at 25 ± 1° C. and 80 ± 2% RH.

Single Crystal X-Ray Diffraction Method of the Present Disclosure

Instrument model: Single crystal X-ray diffractometer (SC-XRD) (D8 VENTURE)

Test method: The sample is dissolved in 1.5 mL of ethyl acetate at room temperature. The sample solution is placed in a 1 mL semi-sealed centrifuge tube and allowed to stand in a place protected from light and vibration. The sample solution is evaporated slowly at room temperature. A colorless needle-like crystal is obtained on day 3. Diffraction experiment temperature T=99.99(11) K.

Instrument Parameters:

Bruker D8 VENTURE CMOS Photon II diffractometer with helios mx multilayer monochrmator.

Cryosystem: Oxford Cryostream 800

Light source: Cu, λ=1.54184 Å, 2.5 kW,

–distance from crystal to CCD detector: d=45 mm

Tube voltage: 50 kV

Tube current: 50 mA

DETAILED DESCRIPTION OF THE PREFERRED EMBODIMENT

Figure 1:
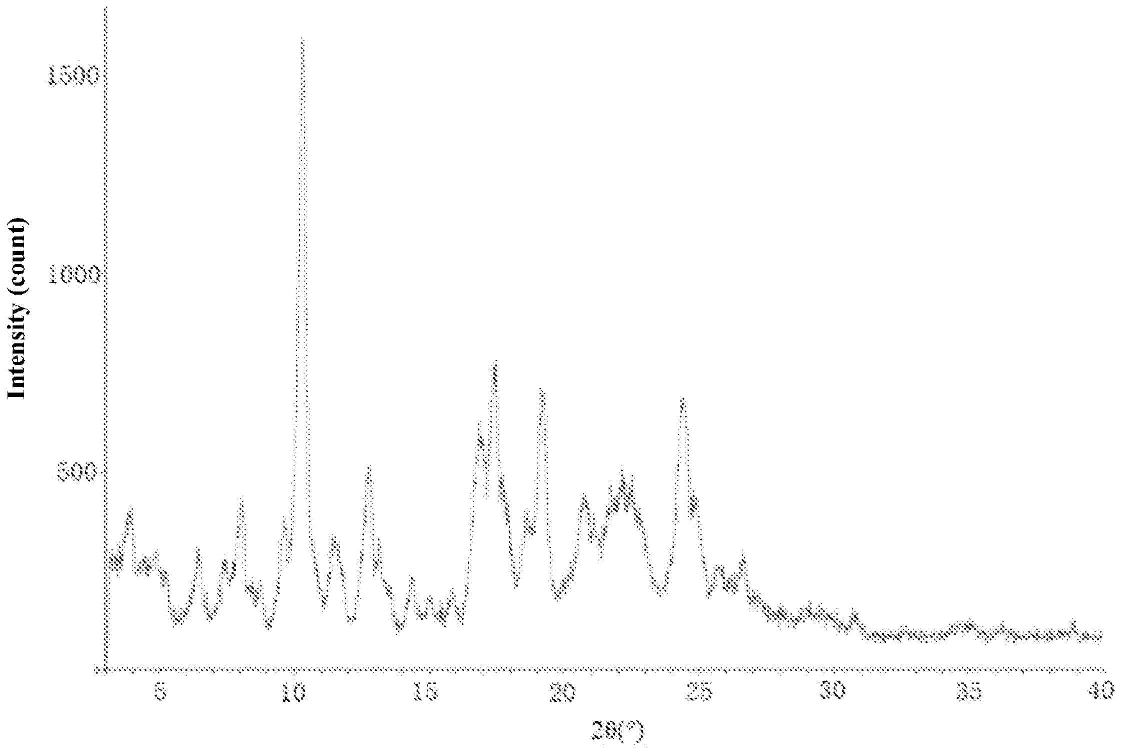
FIG. 1 shows an XRPD pattern with Cu-Kα radiation of the crystal form Q of the compound of formula (I)

The present disclosure is described in detail by the examples below, but it does not mean that there are any adverse restrictions on the present disclosure. The present disclosure has been described in detail herein, and its specific examples have also been disclosed; for one skilled in the art, it is obvious to make various modifications and improvements to the examples of the present disclosure without departing from the spirit and scope of the present disclosure.

Example 1: Preparation of Compound of Formula (I)

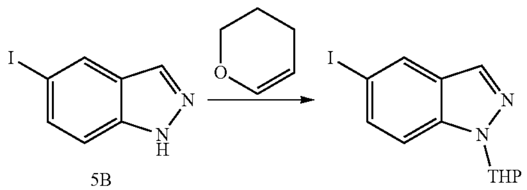

5B

5A

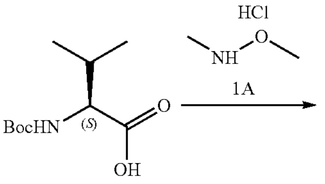

1

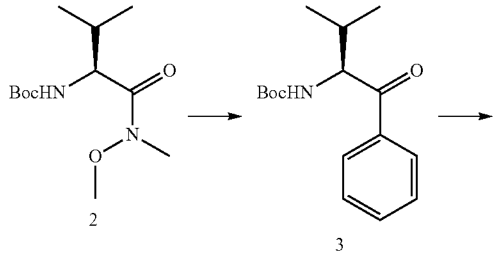

2

3

-continued

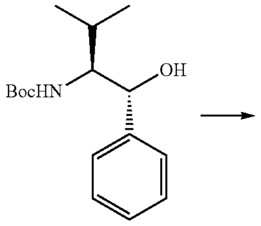

4

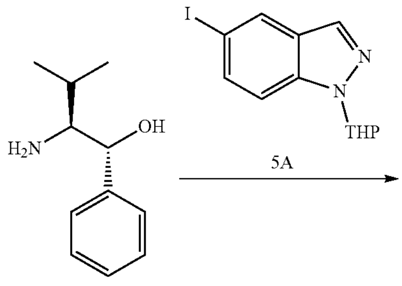

5

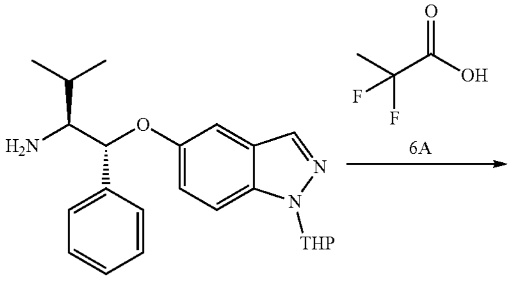

6

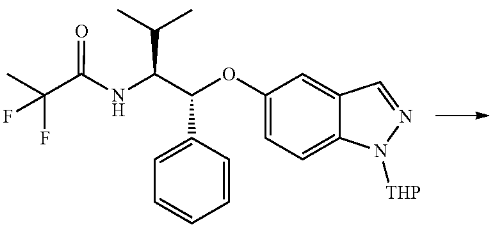

7

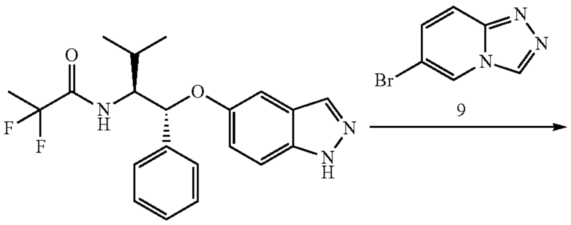

8

-continued

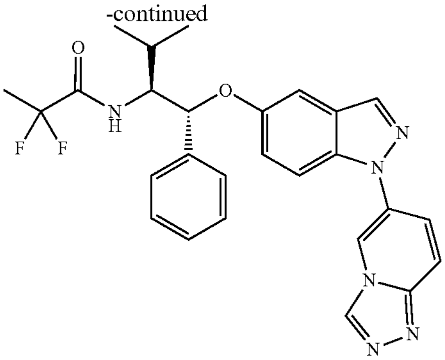

(I)

Step 1: Synthesis of Compound 5A 4-pot parallel reaction: To a dry three-necked flask was added compound 5B (200 g), which was dissolved by adding dichloromethane (2 L), and added with p-toluenesulfonic acid (15.59 g) with stirring. 2,3-Dihydropyran (206.82 g) was slowly added dropwise thereto. After the dropwise addition was completed, the reaction mixture was stirred and reacted at 20° C. for 16 hours. After the reaction was completed, the reaction mixtures in the 4 pots were combined and processed. To saturated sodium bicarbonate solution (8 L) was added the reaction mixture. The phases were separated, and the aqueous phase was extracted with dichloromethane (2 L×2). The organic phases were combined, washed with saturated brine (8 L), dried over anhydrous sodium sulfate, filtered, and the filtrate was concentrated under reduced pressure. The crude product was purified by column chromatography (eluent: petroleum ether/ethyl acetate=1/0 to 5/1, v/v) to obtain compound 5A. 1H NMR (400 MHZ, $CDCl_3$) δ ppm 8.05-8.12 (m, 1H) 7.95 (d, J=0.4 Hz, 1H) 7.58-7.65 (m, 1H) 7.36-7.44 (m, 1H) 5.66-5.75 (m, 1H) 3.96-4.06 (m, 1H) 3.68-3.79 (m, 1H) 2.48-2.60 (m, 1H) 2.02-2.21 (m, 2H) 1.66-1.79 (m, 3H).

Step 2: Synthesis of Compound 2

To a dry 50 L reaction kettle was added dichloromethane (15 L), then added compound 1 (1.5 kg) in batches, and the reaction mixture was stirred until it became clarified. To the reaction kettle was then added N,N'-carbonyldiimidazole (1.4 kg) in batches. After the addition was completed, the reaction mixture was stirred at 20° C. for 4 hours. To the reaction system was added N-methylmorpholine (1.0 kg), and then added compound 1A (0.84 kg) in batches. After the addition was completed, the reaction mixture was stirred and reacted at 20° C. for 12 hours. After the reaction was completed, the reaction mixture was transferred to a separatory funnel, and water (20 L) was added thereto. The phases were separated, and the organic phase was collected. The organic phase was sequentially washed with saturated citric acid aqueous solution (20 L×3) and saturated sodium bicarbonate aqueous solution (20 L×2), and dried over anhydrous sodium sulfate. The organic phase was filtered, and the filtrate was concentrated under reduced pressure to obtain compound 2.

Step 3: Synthesis of Compound 3

To a 50 L reaction kettle was added anhydrous tetrahydrofuran (16 L), then the stirring was started, and compound 2 (1.6 kg) was added thereto. The system was cooled to −10° C., and isopropylmagnesium chloride (574.4 g, 2 mol/L tetrahydrofuran solution) was added dropwise thereto at a controlled temperature of −10 to −5° C. After the dropwise addition was completed, the reaction mixture was maintained at −10° C. and stirred for 0.5 hours. To the reaction system was added dropwise phenylmagnesium bromide (1672 g, 3 mol/L ether solution) at −10 to −5° C. After the dropwise addition was completed, the reaction mixture was warmed to 25° C. and stirred for 12 hours. After the reaction was completed, the reaction mixture was slowly added with saturated ammonium chloride solution (15 L) and ice water (3 L) to quench. The phases were separated, then the organic phase was collected, and the aqueous phase was extracted with ethyl acetate (10 L×2). The organic phases were combined, dried over anhydrous sodium sulfate, filtered, and the filtrate was concentrated under reduced pressure to obtain compound 3.

Step 4: Synthesis of Compound 4

To a 50 L reaction kettle was added isopropanol (15 L), and added a solution of compound 3 (1.7 kg) in isopropanol (2 L). To the system was then added aluminum isopropoxide (625.88 g) to obtain a gray suspension. After the addition was completed, the reaction mixture was heated to 50° C. and stirred and reacted for 12 hours. After the reaction was completed, the reaction mixture was concentrated under reduced pressure to remove most of the isopropanol. The residue was dissolved in ethyl acetate (5 L), added with saturated citric acid aqueous solution (20 L) to adjust the pH to 3 to 4, and then extracted with ethyl acetate (10 L×3). The organic phases were combined, dried over anhydrous sodium sulfate, filtered, and the filtrate was concentrated under reduced pressure to obtain compound 4 as a red oil.

Step 5: Synthesis of Hydrochloride of Compound 5

To hydrochloric acid/ethyl acetate (4 mol/L, 12 L) was added compound 4 (1.5 kg) in batches, and the reaction mixture was stirred at 20° C. for 16 hours. After the reaction was completed, the reaction system was added with methyl tert-butyl ether (10 L) and stirred for 2 hours. A large amount of solid was precipitated. The reaction mixture was filtered. The filter cake was rinsed with methyl tert-butyl ether (5 L) in batches, collected, and dried under vacuum to obtain the hydrochloride of compound 5 as a white solid. $^1$H NMR (400 MHZ, DMSO-$d_6$) δ ppm 8.08 (br s, 3H) 7.41-7.45 (m, 2H) 7.36 (t, J=7.45 Hz, 2H) 7.25-7.31 (m, 1H) 6.09 (d, J=3.95 Hz, 1H) 5.02 (t, J=3.51 Hz, 1H) 1.66-1.77 (m, 1H) 0.91-0.95 (m, 3H) 0.85-0.89 (m, 3H).

Step 6: Synthesis of Compound 6

10-pot parallel reaction: To acetonitrile (1.5 L) was added the hydrochloride of compound 5 (100 g), then added cesium carbonate (302.1 g), and sequentially added compound 5A (101.4 g) and N,N-dimethylglycine (31.9 g). The reaction system was replaced with nitrogen three times, finally added with cuprous iodide (11.8 g), then replaced with nitrogen three times, and stirred in an oil bath at 110° C. for 72 hours. After the reaction was completed, the reaction mixture was cooled to room temperature, and the reaction mixtures in the 10 pots were combined and processed. The reaction mixture was filtered, then the filter cake was rinsed with ethyl acetate (5 L) in batches, and the filtrate was concentrated to dryness under reduced pressure. The residue was dissolved in methyl tert-butyl ether (10 L), and saturated citric acid aqueous solution (15 L) was added thereto. The reaction mixture was stirred, and then the phases were separated. The aqueous phase was extracted with methyl tert-butyl ether (10 L). The aqueous phase was retained and the organic phase was discarded. The aqueous phase was added with sodium hydroxide aqueous solution (1 mol/L) to adjust the pH to 7 to 8, then added with ammonia water to adjust the pH to 8 to 9, and extracted with ethyl acetate (10 L×3). The organic phases were combined, dried over anhydrous sodium sulfate, filtered, and the filtrate was concentrated to dryness under reduced pressure. The crude product was purified by column chromatography (eluent: n-heptane/ethyl acetate=1/1 to 0/1) to obtain compound 6 as a red solid.

Step 7: Synthesis of Compound 7

2-pot parallel reaction: To a dry 5 L three-necked flask was added ethyl acetate (2 L), and then added compound 6 (250 g) and compound 6A (79.75 g). The reaction mixture was cooled to 10° C. or less in an ice-water bath, then a solution of propylphosphonic anhydride in 50% ethyl acetate (628.83 g) was added dropwise thereto in batches at a controlled temperature T below 10° C., and finally N-methylmorpholine (133.27 g) was added dropwise thereto at a controlled temperature T below 10° C. After the dropwise addition was completed, the reaction mixture was warmed to 20° C. and stirred for 16 hours. After the reaction was completed, the reaction mixtures in the 2 pots were combined and processed. The reaction mixture was added with water (4 L), stirred, and then the phases were separated. The aqueous phase was extracted with ethyl acetate (2 L×2). The organic phases were combined, washed with saturated sodium bicarbonate aqueous solution (4 L) and saturated brine (4 L), respectively, and concentrated to dryness under reduced pressure to obtain compound 7 as a light yellow solid.

Step 8: Synthesis of Hydrochloride of Compound 8

To a dry 3 L three-necked flask was added hydrogen chloride/methanol solution (4 mol/L, 2 L), and added compound 7 (200 g) in batches. After the addition was completed, the reaction mixture was stirred at 25° C. for 16 hours. After the reaction was completed, the reaction mixture was concentrated under reduced pressure to remove methanol. The residue was dissolved in ethyl acetate (1 L), and n-heptane (1.5 L) was slowly added dropwise thereto. A solid was slowly precipitated from the system, and the reaction mixture was stirred for another 2 hours. The reaction mixture was filtered, and the resulting solid was rinsed with ethyl acetate:n-heptane=1:1.5 (500 mL). The solid was collected and dried under vacuum to obtain the hydrochloride of compound 8.

Step 9: Synthesis of Compound of Formula (I)

To a dry 3 L three-necked flask was added 1,4-dioxane (2.25 L), then added the hydrochloride of compound 8 (150 g), and the stirring was started. Potassium carbonate (146.72 g) was then added thereto, and the reaction mixture was stirred for 10 minutes. Compound 9 (84.09 g) and (1R,2R)-(−)-N,N-dimethylcyclohexane-1,2-diamine (25.17 g) were added thereto, and the reaction mixture was replaced with nitrogen three times. Cuprous iodide (13.48 g) was finally added thereto, and the reaction mixture was replaced with nitrogen three times. The reaction mixture was heated to 110° C. and reacted for 36 hours under nitrogen atmosphere. After the reaction was completed, the reaction mixture was cooled to room temperature, then filtered through diatomite, and the filter cake was rinsed with ethyl acetate (1 L). The filtrate was washed once with a mixture of water (3 L) and ammonia water (300 mL), and the phases were separated; the aqueous phase was extracted with ethyl acetate (2 L×2). The organic phases were combined, washed once with saturated brine (3 L), and concentrated to dryness under reduced pressure to obtain a crude product. The crude product was dissolved in dichloromethane, filtered through a silica gel pad (100 to 200 mesh silica gel, 1:3 w/w), and eluted with dichloromethane:methanol=50:1. The eluent was concentrated to dryness under reduced pressure, and the resulting crude product was recrystallized with ethanol (1.25 L) to obtain a crude product (I). The crude product (I) was purified by preparative chromatography (column type: Phenomenex luna C18 250 mm*100 mm*10 μm; mobile phase: [$H_2O$ (0.05% HCl)-ACN]; ACN %: 30% to 60%, 20 min). The prepared solution was concentrated under reduced pressure to remove most of the acetonitrile, added with saturated sodium bicarbonate solution to adjust the pH to 7 to 8, and extracted with ethyl acetate (1 L×2). The organic phases were combined and concentrated to dryness under reduced pressure to obtain the compound of formula (I) (76 g).

Example 2: Preparation of Crystal Form Q of Compound of Formula (I)

Figure 2:
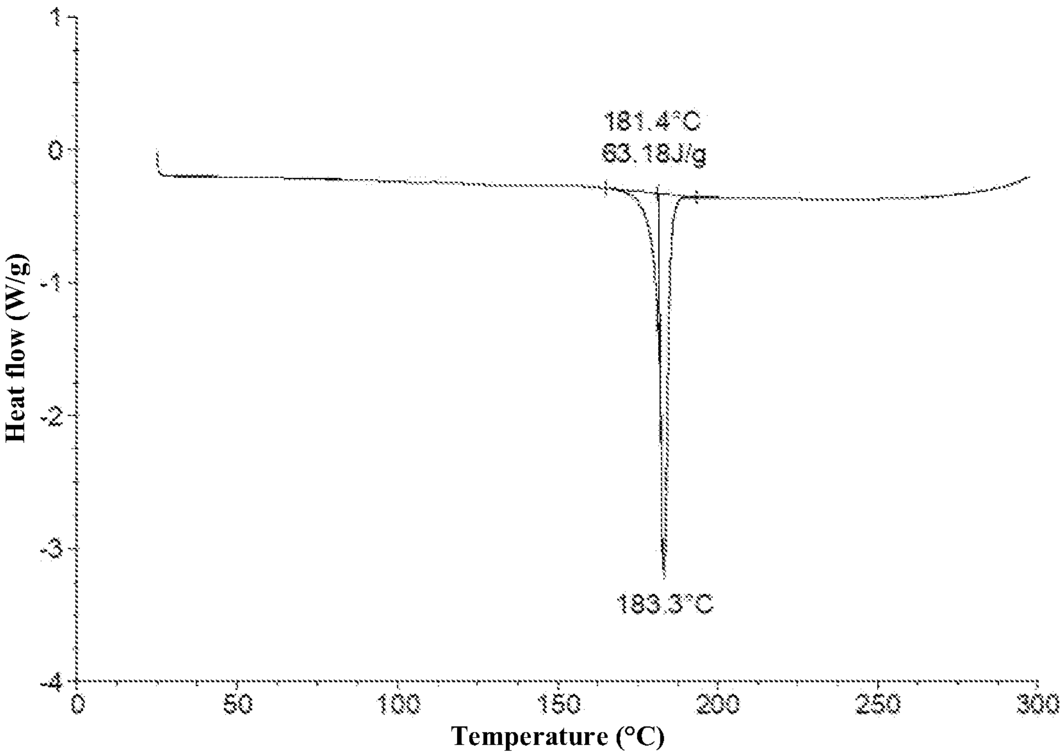
FIG. 2 shows a DSC pattern of the crystal form Q of the compound of formula (I)
Figure 3:
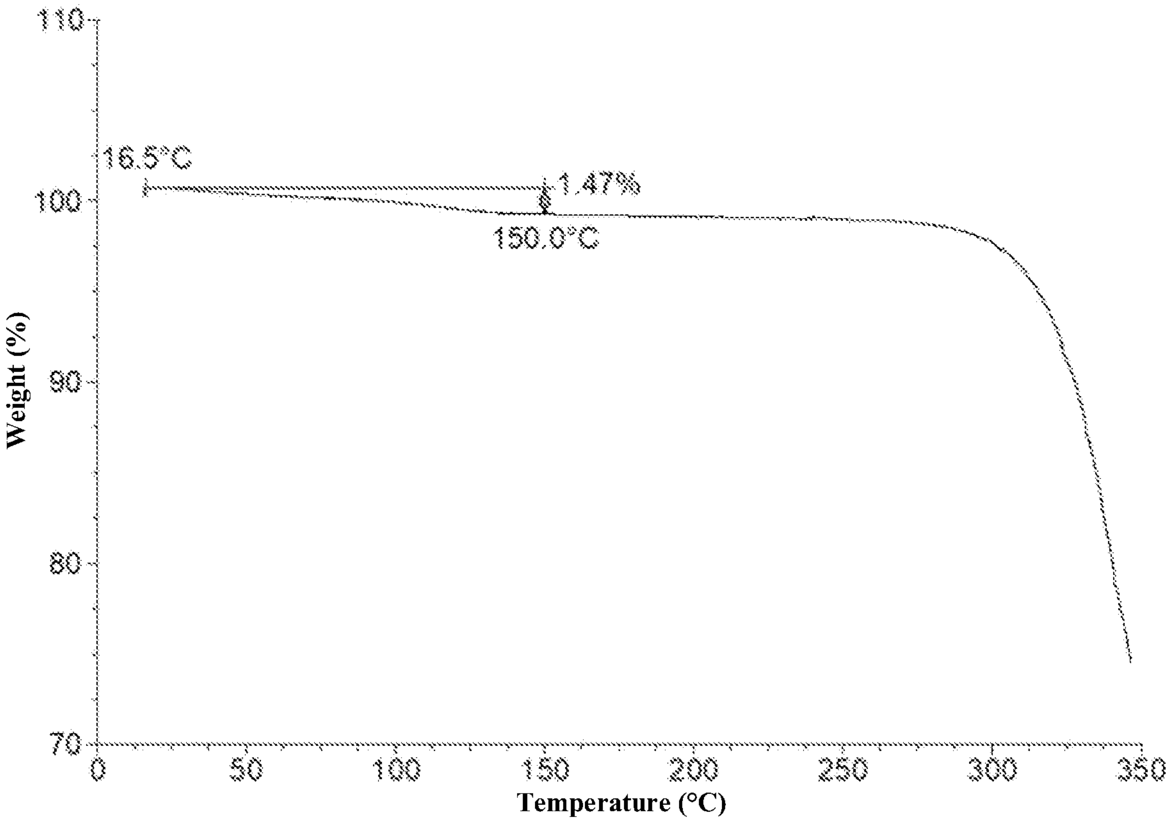
FIG. 3 shows a TGA pattern of the crystal form Q of the compound of formula (I)

To a dry 5 L three-necked flask was added a mixed solvent of methyl isobutyl ketone:n-heptane=1:6 (1.9 L), and added the compound of formula (I) (76 g) in batches. After the addition was completed, the reaction mixture was heated to 50° C. and stirred for 96 hours. The reaction mixture was filtered, and the filter cake was rinsed with methyl isobutyl ketone:n-heptane=1:6 (300 mL). The solid was collected and dried under vacuum at 60° C. to obtain the crystal form Q of the compound of formula (I). 1H NMR (400 MHZ, DMSO-$d_6$) δ ppm 9.28 (s, 1H) 9.07 (d, J=0.88 Hz, 1H) 8.23-8.32 (m, 2H) 7.95 (d, J=9.8 Hz, 1H) 7.76-7.89 (m, 2H) 7.50 (d, J=7.16 Hz, 2H) 7.27-7.34 (m, 2H) 7.19-7.26 (m, 2H) 7.17 (d, J=2.14 Hz, 1H) 5.33 (d, J=9.54 Hz, 1H) 4.24 (td, J=9.69, 4.08 Hz, 1H) 2.43 (td, J=6.84, 4.28 Hz, 1H) 1.39 (t, J=19.46 Hz, 3H) 0.93 (t, J=6.28 Hz, 6H). For the crystal form Q, the XRPD pattern is shown in FIG. 1, the DSC pattern is shown in FIG. 2, and the TGA pattern is shown in FIG. 3.

Example 3: Preparation of Crystal Form S of Compound of Formula (I)

250 mg of the compound of formula (I) was weighed and added to a 10 mL single-necked flask, and ethyl acetate (1.75 mL) was added thereto at 20° C. to make a suspension. After adding the magneton, the above suspension sample was stirred on a magnetic stirrer with heating (80° C.) until completely dissolved. The reaction mixture was then slowly cooled to 20° C. to precipitate a solid. The reaction mixture was filtered under reduced pressure under $N_2$ atmosphere, and the resulting solid was dried under vacuum to obtain the crystal form S of the compound of formula (I).

To a 100 mL single-necked flask was added the compound of formula (I) (4 g) at 20° C., and added ethyl acetate (28 mL) to make a suspension. After adding the magneton, the above suspension sample was stirred on a magnetic stirrer with heating (80° C.) until completely dissolved, and stirred for another 1 hour. The reaction mixture was then slowly cooled to 20° C. to precipitate a solid. The reaction mixture was filtered under reduced pressure under $N_2$ atmosphere, and the filter cake was dried to constant weight in a vacuum drying oven to obtain the crystal form S of the compound of formula (I).

Figure 5:
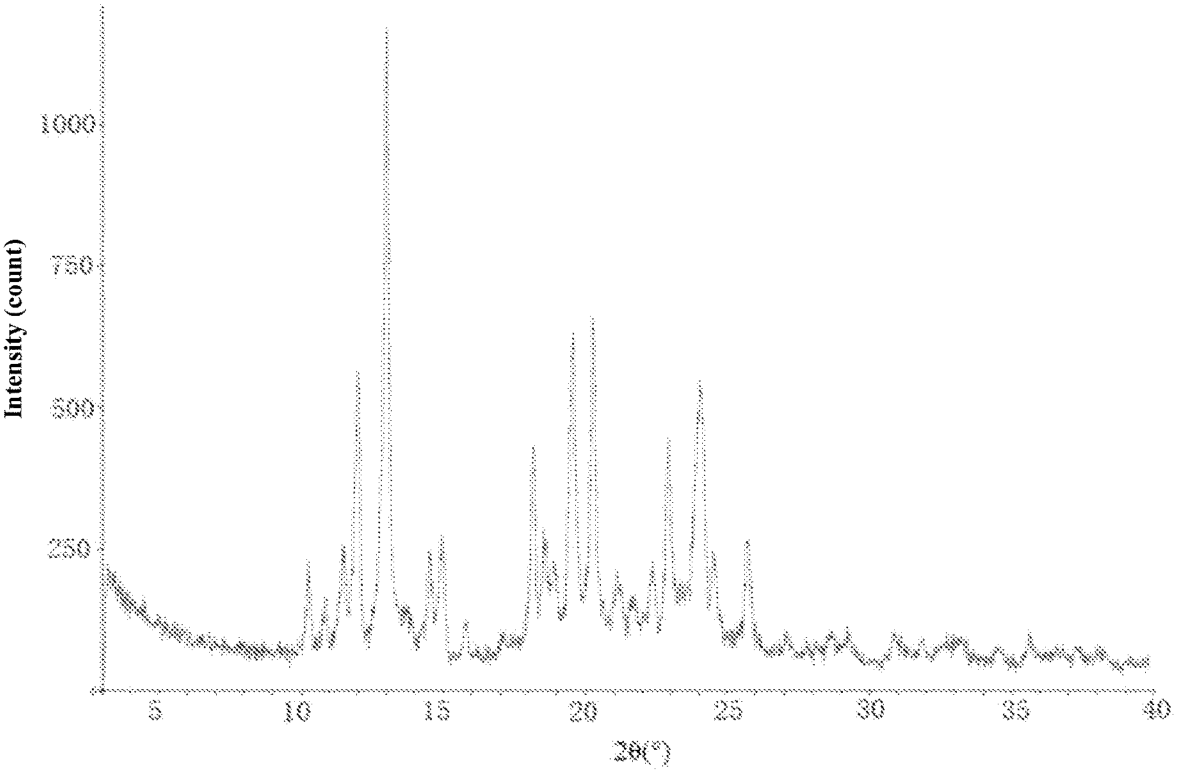
FIG. 5 shows an XRPD pattern with Cu-Kα radiation of the crystal form S of the compound of formula (I)
Figure 6:
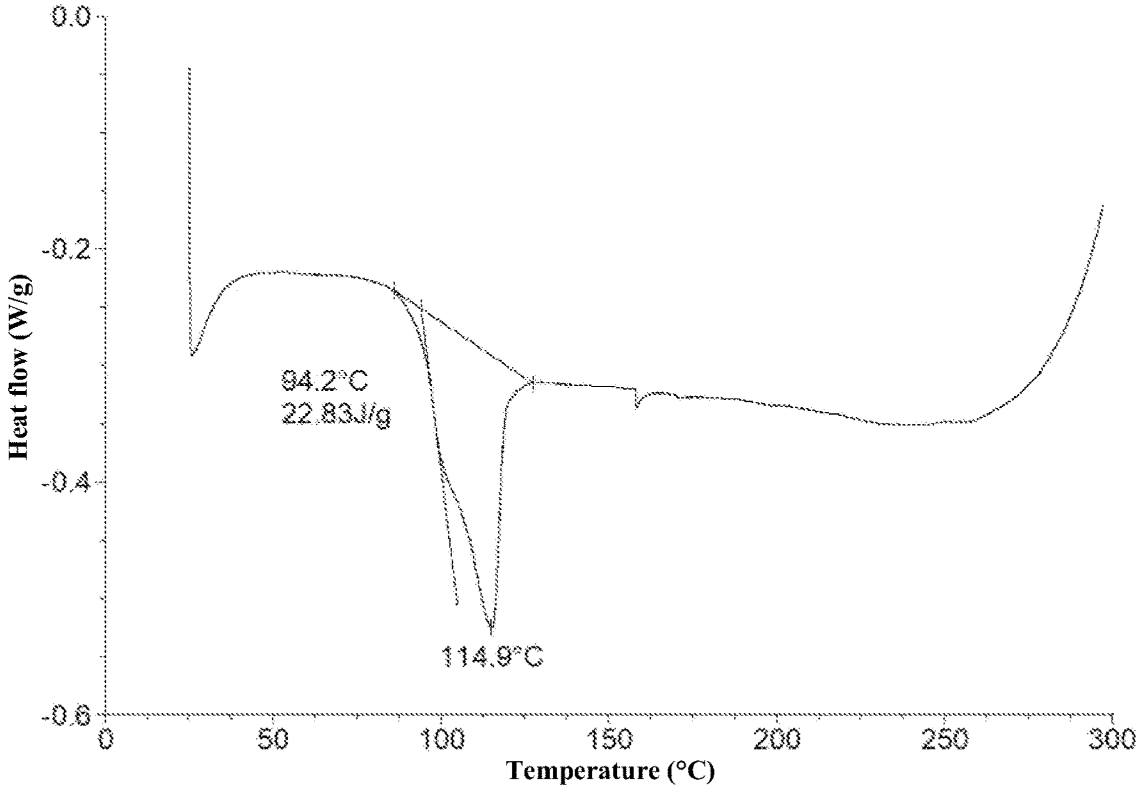
FIG. 6 shows a DSC pattern of the crystal form S of the compound of formula (I)
Figure 7:
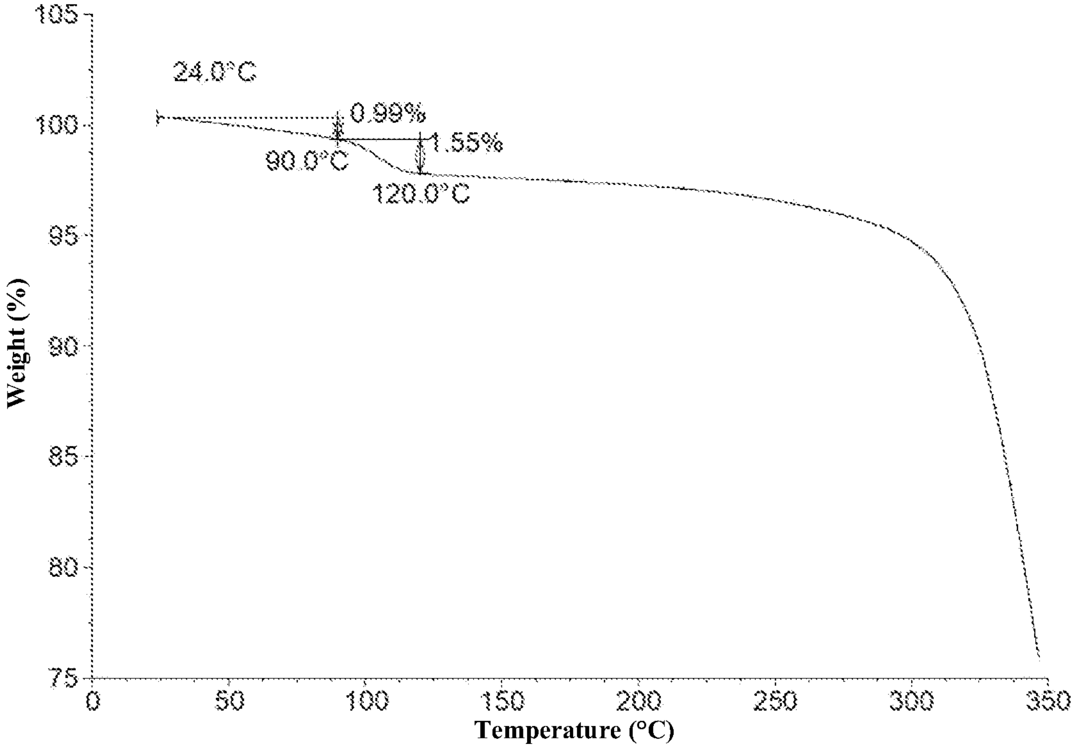
FIG. 7 shows a TGA pattern of the crystal form S of the compound of formula (I)

$^1H$ NMR (400 MHZ, DMSO-$d_6$) δ ppm 9.27 (s, 1H) 9.07 (s, 1H) 8.24-8.32 (m, 2H) 7.95 (d, J=9.88 Hz, 1H) 7.78-7.89 (m, 2H) 7.50 (d, J=7.46 Hz, 2H) 7.26-7.34 (m, 2H) 7.18-7.26 (m, 2H) 7.17 (d, J=2.20 Hz, 1H) 5.33 (d, J=9.66 Hz, 1H) 4.23 (td, J=9.66, 4.18 Hz, 1H) 2.43 (td, J=6.63, 4.28 Hz, 1H) 1.39 (t, J=19.40 Hz, 3H) 0.92 (t, J=6.26 Hz, 6H). For the crystal form S, the XRPD pattern is shown in FIG. 5, the DSC pattern is shown in FIG. 6, and the TGA pattern is shown in FIG. 7.

Example 4: Study on Hygroscopicity of Crystal Form Q of Compound of Formula (I)

Experimental Materials:

SMS DVS Advantage dynamic vapor sorption analyzer

Experimental Methods:

10 to 15 mg of the crystal form Q of the compound of formula (I) was taken and placed in a DVS sample disk for testing.

Figure 4:
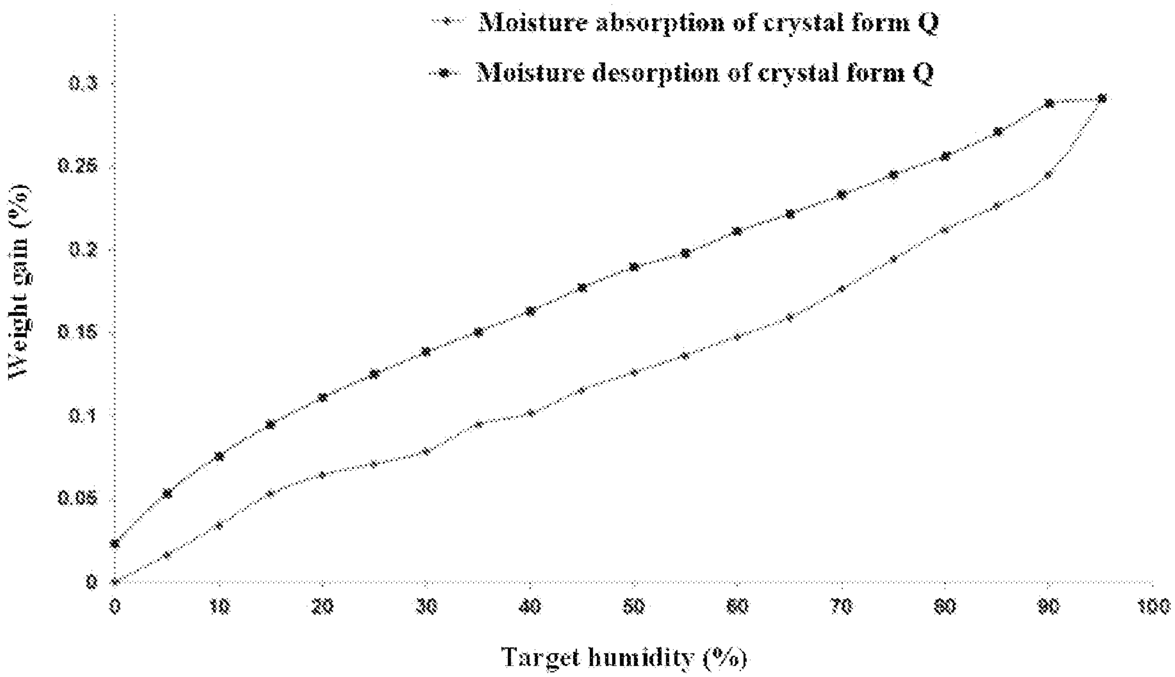
FIG. 4 shows a DVS pattern of the crystal form Q of the compound of formula (I)

Experimental Results:

The DVS pattern of the crystal form Q of the compound of formula (I) is shown in FIG. 4 with a ΔW of 0.21%.

Experimental Conclusion:

The sample of the crystal form Q of the compound of formula (I) is slightly hygroscopic at 25° C. with a hygroscopic weight gain of 0.21% at 80% RH compared to initial 0% RH.

Example 5: Study on Hygroscopicity of Crystal Form S of Compound of Formula (I)

Experimental Materials:

SMS DVS Advantage dynamic vapor sorption analyzer

Experimental Methods:

10 to 15 mg of the crystal form S of the compound of formula (I) was taken and placed in a DVS sample disk for testing.

Figure 8:
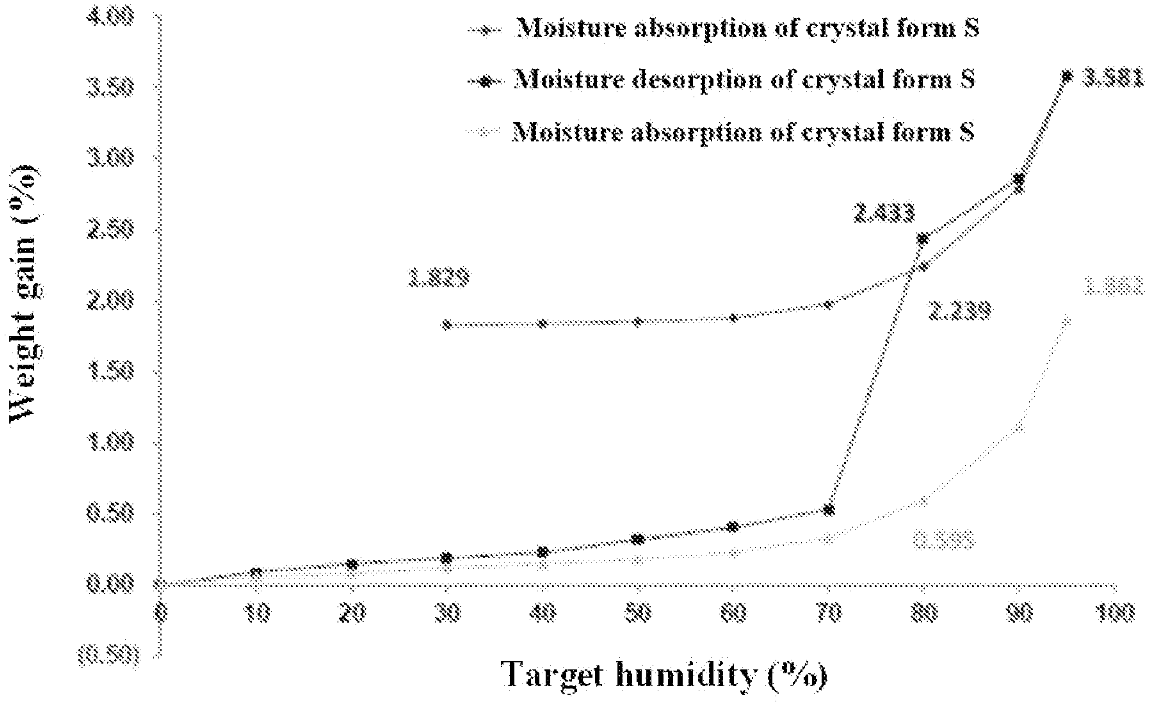
FIG. 8 shows a DVS pattern of the crystal form S of the compound of formula (I)

Experimental Results:

The DVS pattern of the crystal form S of the compound of formula (I) is shown in FIG. 8 with the sample having a hygroscopic weight gain (ΔW) of 0.6% at 80% RH compared to 0% RH.

Experimental Conclusion:

The sample of the crystal form S of the compound of formula (I) is slightly hygroscopic at 25° C. with a hygroscopic weight gain of 0.6% at 80% RH compared to initial 0% RH.

Example 6: Solid Stability Test of Crystal Form Q of Compound of Formula (I)

Based on the "Guideline for Stability Testing of Active Pharmaceutical Ingredients and Preparations" (Chinese Pharmacopoeia 2015 Edition, Volume IV, General Rule 9001), the stability of the crystal form Q of the compound of formula (I) was investigated under high temperature (60° C., open), high humidity (room temperature/relative humidity: 92.5%, open), and strong light (5000 lx, sealed) conditions.

15 mg of the crystal form Q of the compound of formula (I) was weighed and placed at the bottom of a glass sample vial, and spread into a thin layer. For samples placed under high temperature and high humidity conditions, the vial was sealed with aluminum foil punched with small holes to ensure that the samples could fully contact with the ambient air; for samples placed under strong light conditions, the vial was sealed with a threaded cap. The samples placed under different conditions were sampled and detected (XRPD) on day 5, day 10, and month 3, and the results were compared with the initial results on day 0. The test results are shown in Table 4 below:

TABLE 4

| Solid stability test results of crystal form Q of compound of formula (I) | | |
|---|---|---|
| Test conditions | Time point | Crystal form |
| — | Day 0 | Crystal form Q |
| High temperature (60° C., open) | Day 5 | Crystal form Q |
| | Day 10 | Crystal form Q |
| | Month 3 | Crystal form Q |
| High humidity (room temperature/relative humidity: 92.5%, open) | Day 5 | Crystal form Q |
| | Day 10 | Crystal form Q |
| | Month 3 | Crystal form Q |
| Strong light (5000 lx, sealed) | Day 5 | Crystal form Q |
| | Day 10 | Crystal form Q |
| | Month 3 | Crystal form Q |

Conclusion: The crystal form Q of the compound of formula (I) has good stability under high temperature, high humidity, and strong light conditions.

Example 7: Single Crystal X-Ray Diffraction Detection Analysis of Compound of Formula (I)

Single crystal culture process: The sample was dissolved in 1.5 mL of ethyl acetate at room temperature. The sample solution was placed in a 1 mL semi-sealed centrifuge tube and allowed to stand in a place protected from light and vibration. The sample solution was evaporated slowly at room temperature. A colorless needle-like crystal was obtained on day 3.

Figure 9:
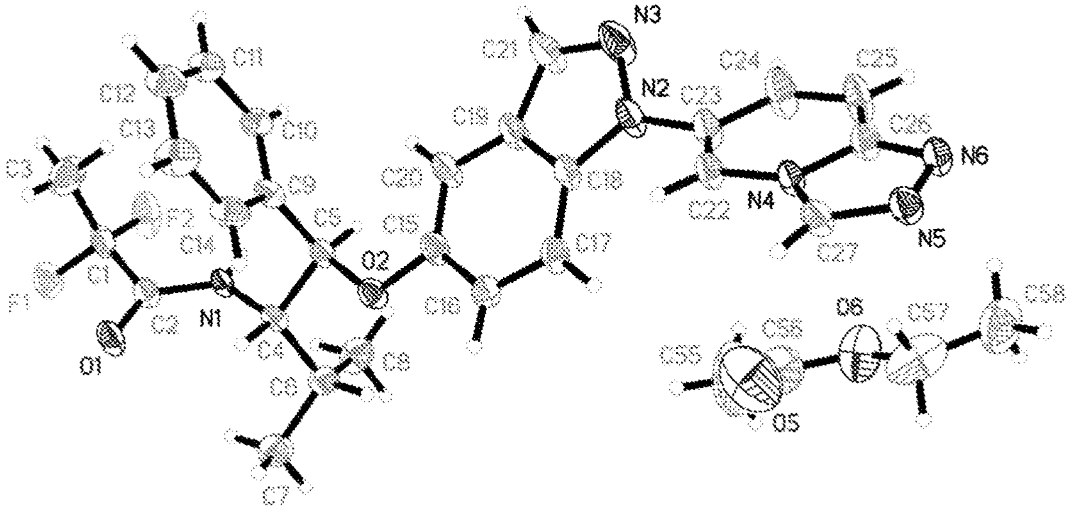
FIG. 9 shows an ellipsoid diagram of the three-dimensional structure of the compound of formula (I)
Figure 10:
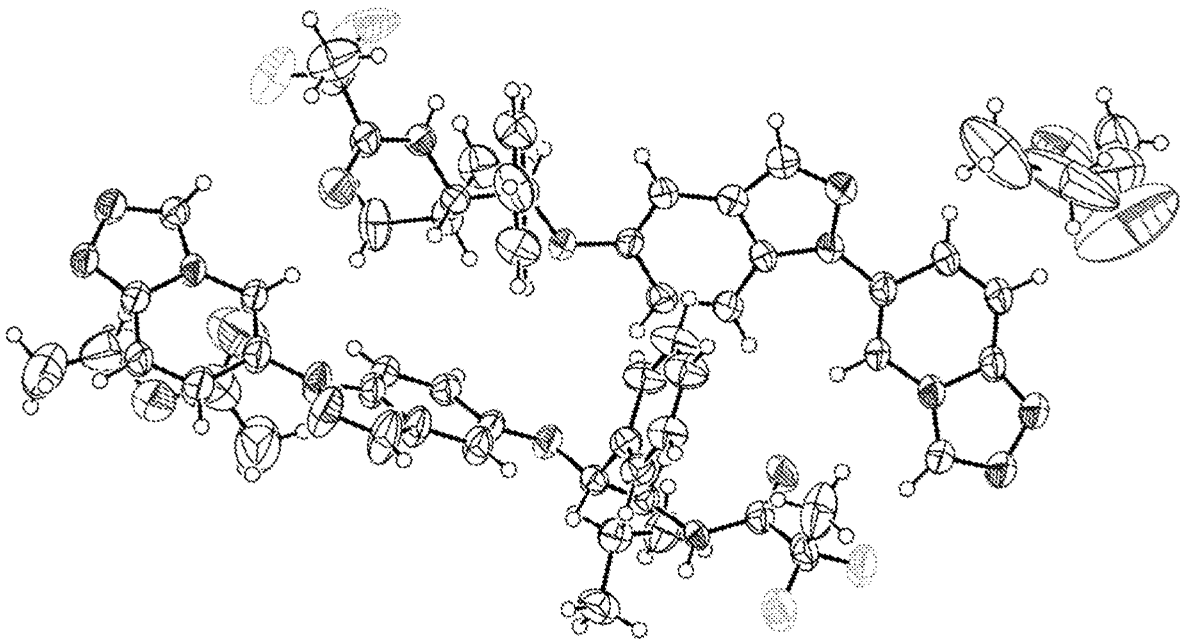
FIG. 10 shows an ellipsoid diagram of the three-dimensional structure of two molecules of the single unit cell of the compound of formula (I).

Analyzed by single crystal X-ray diffraction detection, one unit cell obtained contained two molecules of the compound of formula (I) and two molecules of the solvent (ethyl acetate). The ellipsoid diagrams of the three-dimensional structure of the compound of formula (I) are shown in FIGS. 9 and 10. The crystal structure data and parameters of the compound of formula (I) are shown in Tables 5, 6, 7, 8, and 9.

TABLE 5

| Crystal data of compound of formula (I) | |
|---|---|
| Crystal Size | 0.200 × 0.180 × 0.160 $mm^3$ |
| Wavelength | $\lambda$ = 1.54178 Å |
| Crystal system | Monoclinic |
| Space Group | P2(1) |
| Cell Size | a = 8.6018(5) Å |
| | b = 24.3321(15) Å |
| | c = 16.4763(9) Å |
| | $\alpha$ = 90° |
| | $\beta$ = 105.13° |
| | $\gamma$ = 90° |
| Cell Volume | V = 3328.9(3) $Å^3$ |
| Cell Formula Units | Z = 4 |
| Crystal Density | $D_c$ = 1.182 $Mg/m^3$ |
| Crystal F(000) | 1248 |
| Absorption Coefficient | $\mu$ (Cu K$\alpha$) = 0.728 $mm^{-1}$ |
| Limiting Indices | $-10 \le h \le 10$ |
| | $-29 \le k \le 29$ |
| | $-19 \le l \le 19$ |
| Cell Measurement Temperature | T = 99.99 (11) K. |
| 2$\theta$ range for data collection | 3.32 to 69.029° |
| Goodness-of-fit on F^2 | 1.022 |
| Final R indices [I > 2sigma(I)] | R1 = 0.0728, wR2 = 0.1963 |
| R indices (all data) | R1 = 0.0928, wR2 = 0.2170 |
| Largest diff. peak and hole | 0.484 and −0.347 e · $Å^{-3}$ |
| Reflections collected/unique | 52538/12223 [$R_{(int)}$ = 0.0760] |

TABLE 6

| Atomic coordinates ($\times 10^4$) and equivalent isotropic displacement parameters ($Å^2 \times 10^3$) of crystals of compound of formula (I) | | | | |
|---|---|---|---|---|
| | x | y | z | U(eq) |
| C(1) | 3756(7) | 2316(3) | 1212(4) | 54(1) |
| F(1) | 2413(5) | 2020(2) | 842(2) | 66(1) |
| N(1) | 4275(5) | 2931(2) | 2401(2) | 37(1) |
| O(1) | 2099(5) | 3082(2) | 1271(2) | 58(1) |
| O(2) | 5624(4) | 4242(2) | 3388(2) | 45(1) |
| F(2) | 4723(6) | 1973(2) | 1765(3) | 86(1) |
| C(2) | 3281(7) | 2808(2) | 1643(3) | 45(1) |
| N(2) | 11047(6) | 5448(2) | 4840(4) | 64(2) |
| N(6) | 12735(6) | 7349(2) | 6640(3) | 48(1) |
| O(6) | 9308(10) | 6241(3) | 7491(4) | 102(2) |
| C(6) | 3550(7) | 3376(3) | 3625(4) | 50(1) |
| N(5) | 11511(6) | 7676(2) | 6158(3) | 51(1) |
| O(5) | 7724(13) | 6394(5) | 6218(7) | 160(4) |
| C(5) | 5850(6) | 3726(2) | 3001(3) | 38(1) |
| N(4) | 11160(5) | 6846(2) | 5625(3) | 43(1) |
| F(4) | 7645(9) | 8034(3) | 3867(5) | 127(2) |
| O(4) | 3493(5) | 5682(2) | 2182(2) | 45(1) |
| C(4) | 4176(6) | 3441(2) | 2833(3) | 39(1) |
| N(3) | 12265(7) | 5130(3) | 4685(5) | 87(2) |
| F(3) | 5977(6) | 8022(2) | 2627(6) | 2627(6) |
| O(3) | 7817(6) | 6920(2) | 3812(4) | 78(2) |
| C(3) | 4588(12) | 2479(4) | 545(6) | 94(3) |
| C(8) | 4346(10) | 2907(3) | 4195(4) | 67(2) |
| N(8) | 607(7) | 4885(2) | −1297(3) | 56(1) |
| C(7) | 1746(9) | 3283(3) | 3358(5) | 65(2) |
| O(7) | −3050(40) | 3459(8) | −4040(20) | 361(17) |
| C(62) | 630(18) | 4364(10) | −3612(9) | 184(9) |
| C(61) | −645(18) | 3894(13) | −4107(15) | 261(16) |
| C(60) | −4847(13) | 4198(5) | −4140(7) | 109(3) |
| C(59) | −3424(19) | 3894(7) | −4209(9) | 126(4) |
| N(7) | 5323(5) | 7003(2) | 2890(3) | 46(1) |
| C(9) | 6341(6) | 3801(2) | 2201(3) | 43(1) |
| C(11) | 7919(8) | 3559(3) | 1257(4) | 56(2) |
| N(11) | −1982(7) | 2284(2) | −776(4) | 63(1) |
| C(10) | 7498(7) | 3480(2) | 2004(4) | 46(1) |
| O(10) | −2087(11) | 4225(5) | −3918(5) | 127(3) |
| N(10) | −883(6) | 3103(2) | −673(3) | 45(1) |
| N(12) | −2785(7) | 2582(2) | −1476(3) | 60(1) |
| C(12) | 7172(8) | 3952(3) | 702(4) | 66(2) |
| C(13) | 5972(9) | 4283(3) | 889(5) | 73(2) |
| C(14) | 5578(7) | 4207(3) | 1634(4) | 58(2) |
| C(15) | 7017(7) | 4542(2) | 3738(4) | 47(1) |
| C(16) | 6742(7) | 5038(2) | 4107(3) | 45(1) |
| C(18) | 9549(7) | 5218(2) | 4487(4) | 49(1) |
| C(17) | 8002(7) | 5381(2) | 4504(4) | 48(1) |
| C(19) | 9815(7) | 4731(3) | 4112(4) | 59(2) |
| C(20) | 8527(7) | 4377(3) | 3719(4) | 57(2) |
| C(21) | 11524(8) | 4706(4) | 4249(6) | 88(3) |
| C(22) | 10634(7) | 6391(2) | 5123(4) | 47(1) |
| C(23) | 11471(8) | 5921(3) | 5344(4) | 57(2) |
| C(26) | 12504(7) | 6847(2) | 6303(4) | 49(1) |
| C(25) | 13358(9) | 6352(3) | 6530(5) | 69(2) |
| C(24) | 12865(10) | 5901(3) | 6053(5) | 79(2) |
| C(27) | 10585(7) | 7374(2) | 5562(4) | 47(1) |
| C(28) | 7236(8) | 7752(3) | 3083(6) | 75(2) |
| C(29) | 6786(7) | 7183(3) | 3298(4) | 56(2) |
| C(30) | 8656(12) | 7779(4) | 2727(7) | 97(3) |
| C(31) | 4770(7) | 6449(2) | 2990(3) | 42(1) |
| C(32) | 4284(7) | 6192(2) | 2108(3) | 42(1) |
| C(33) | 3501(7) | 6449(3) | 3486(4) | 53(1) |
| C(34) | 4207(10) | 6701(4) | 4351(4) | 79(2) |
| C(35) | 1939(8) | 6740(4) | 3028(5) | 71(2) |
| C(36) | 5772(6) | 6108(2) | 1795(3) | 41(1) |
| C(37) | 6221(7) | 6509(3) | 1307(4) | 52(1) |
| C(38) | 7650(9) | 6455(4) | 1078(4) | 70(2) |
| C(39) | 8601(8) | 6000(4) | 1321(4) | 73(2) |
| C(40) | 8143(8) | 5593(4) | 1796(5) | 69(2) |
| C(41) | 6731(8) | 5649(3) | 2036(4) | 57(2) |
| C(42) | 2592(7) | 5600(2) | 655(3) | 46(1) |
| C(43) | 2698(7) | 5409(2) | 1454(3) | 41(1) |
| C(44) | 1980(6) | 4910(2) | 1584(3) | 44(1) |
| C(45) | 1226(7) | 4572(2) | 937(3) | 44(1) |
| C(46) | 1133(6) | 4756(2) | 121(3) | 43(1) |
| C(47) | 1763(7) | 5262(2) | −23(3) | 48(1) |

TABLE 6-continued

Atomic coordinates (×$10^4$) and equivalent isotropic displacement parameters ($Å^2$ × $10^3$) of crystals of compound of formula (I)

| | x | y | z | U(eq) |
|---|---|---|---|---|
| C(48) | 1434(9) | 5305(3) | −903(4) | 59(2) |
| C(49) | 0(6) | 3577(2) | −426(3) | 43(1) |
| C(50) | −376(6) | 4027(2) | −904(3) | 45(1) |
| C(51) | −1621(7) | 4010(3) | −1688(4) | 54(1) |
| C(52) | −2470(8) | 3541(3) | −1926(4) | 59(2) |
| C(53) | −2129(7) | 3075(3) | −1416(3) | 50(1) |
| C(54) | −861(8) | 2602(2) | −312(4) | 54(1) |
| C(55) | 7750(20) | 5518(6) | 6782(8) | 163(7) |
| C(56) | 8250(13) | 6090(5) | 6791(6) | 99(3) |
| C(57) | 9620(17) | 6789(4) | 7615(8) | 116(4) |
| C(58) | 11011(17) | 6880(5) | 8352(8) | |

TABLE 7

Bond length (Å) of compound of formula (I)

| | Bond length/Å | | Bond length/Å |
|---|---|---|---|
| C(1)—F(2) | 1.350(7) | C(11)—C(10) | 1.384(9) |
| C(1)—F(1) | 1.363(7) | N(11)—C(54) | 1.314(8) |
| C(1)—C(2) | 1.501(9) | N(11)—N(12) | 1.384(8) |
| C(1)—C(3) | 1.513(11) | N(10)—C(54) | 1.355(8) |
| N(1)—C(2) | 1.350(7) | N(10)—C(49) | 1.382(7) |
| N(1)—C(4) | 1.445(7) | N(10)—C(53) | 1.402(7) |
| O(1)—C(2) | 1.236(7) | N(12)—C(53) | 1.320(8) |
| O(2)—C(15) | 1.394(6) | C(12)—C(13) | 1.405(11) |
| O(2)—C(5) | 1.442(6) | C(13)—C(14) | 1.370(10) |
| N(2)—N(3) | 1.378(8) | C(15)—C(20) | 1.368(9) |
| N(2)—C(18) | 1.386(8) | C(15)—C(16) | 1.399(8) |
| N(2)—C(23) | 1.410(7) | C(16)—C(17) | 1.390(8) |
| N(6)—C(26) | 1.336(7) | C(18)—C(19) | 1.383(8) |

TABLE 7-continued

Bond length (Å) of compound of formula (I)

| | Bond length/Å | | Bond length/Å |
|---|---|---|---|
| N(6)—N(5) | 1.391(7) | C(18)—C(17) | 1.397(9) |
| O(6)—C(56) | 1.321(12) | C(19)—C(20) | 1.419(8) |
| O(6)—C(57) | 1.367(13) | C(19)—C(21) | 1.429(10) |
| C(6)—C(7) | 1.515(10) | C(22)—C(23) | 1.351(8) |
| C(6)—C(8) | 1.523(9) | C(23)—C(24) | 1.440(9) |
| C(6)—C(4) | 1.544(8) | C(26)—C(25) | 1.410(9) |
| N(5)—C(27) | 1.315(7) | C(25)—C(24) | 1.353(9) |
| O(5)—C(56) | 1.192(13) | C(28)—C(30) | 1.488(13) |
| C(5)—C(9) | 1.496(8) | C(28)—C(29) | 1.504(10) |
| C(5)—C(4) | 1.557(7) | C(31)—C(33) | 1.525(8) |
| N(4)—C(27) | 1.372(7) | C(31)—C(32) | 1.537(7) |
| N(4)—C(26) | 1.381(7) | C(32)—C(36) | 1.513(8) |
| N(4)—C(22) | 1.384(7) | C(33)—C(34) | 1.524(9) |
| F(4)—C(28) | 1.424(10) | C(33)—C(35) | 1.531(9) |
| O(4)—C(43) | 1.385(6) | C(36)—C(37) | 1.382(8) |
| O(4)—C(32) | 1.436(6) | C(36)—C(41) | 1.384(8) |
| N(3)—C(21) | 1.322(9) | C(37)—C(38) | 1.382(10) |
| F(3)—C(28) | 1.321(9) | C(38)—C(39) | 1.373(12) |
| O(3)—C(29) | 1.234(7) | C(39)—C(40) | 1.382(12) |
| N(8)—C(48) | 1.316(8) | C(40)—C(41) | 1.379(9) |
| N(8)—N(9) | 1.385(7) | C(42)—C(43) | 1.377(8) |
| O(7)—C(59) | 1.12(2) | C(42)—C(47) | 1.421(8) |
| C(62)—C(61) | 1.64(3) | C(43)—C(44) | 1.404(8) |
| C(61)—O(10) | 1.58(3) | C(44)—C(45) | 1.368(8) |
| C(60)—C(59) | 1.460(16) | C(45)—C(46) | 1.399(7) |
| C(59)—O(10) | 1.384(17) | C(46)—C(47) | 1.389(8) |
| N(7)—C(29) | 1.337(7) | C(47)—C(48) | 1.407(8) |
| N(7)—C(31) | 1.451(7) | C(49)—C(50) | 1.339(8) |
| C(9)—C(10) | 1.371(8) | C(50)—C(51) | 1.447(7) |
| C(9)—C(14) | 1.399(8) | C(51)—C(52) | 1.357(9) |
| N(9)—C(46) | 1.401(7) | C(52)—C(53) | 1.395(9) |
| N(9)—C(50) | 1.408(7) | C(55)—C(56) | 1.455(15) |
| C(11)—C(12) | 1.363(9) | C(57)—C(58) | 1.482(16) |

TABLE 8

Bond angle (°) of compound of formula (I)

| | Bond angle/° | | Bond angle/° |
|---|---|---|---|
| F(2)—C(1)—F(1) | 106.0(5) | C(15)—C(20)—C(19) | 116.5(5) |
| F(2)—C(1)—C(2) | 111.7(5) | N(3)—C(21)—C(19) | 112.5(6) |
| F(1)—C(1)—C(2) | 109.3(5) | C(23)—C(22)—N(4) | 116.6(5) |
| F(2)—C(1)—C(3) | 109.1(7) | C(22)—C(23)—N(2) | 119.7(5) |
| F(1)—C(1)—C(3) | 108.6(5) | C(22)—C(23)—C(24) | 121.3(5) |
| C(2)—C(1)—C(3) | 112.0(6) | N(2)—C(23)—C(24) | 118.8(6) |
| C(2)—N(1)—C(4) | 122.8(4) | N(6)—C(26)—N(4) | 109.9(5) |
| C(15)—O(2)—C(5) | 116.0(4) | N(6)—C(26)—C(25) | 131.3(5) |
| O(1)—C(2)—N(1) | 125.4(5) | N(4)—C(26)—C(25) | 118.8(5) |
| O(1)—C(2)—C(1) | 119.0(5) | C(24)—C(25)—C(26) | 118.5(5) |
| N(1)—C(2)—C(1) | 115.4(5) | C(25)—C(24)—C(23) | 120.8(6) |
| N(3)—N(2)—C(18) | 111.4(5) | N(5)—C(27)—N(4) | 109.3(5) |
| N(3)—N(2)—C(23) | 118.4(5) | F(3)—C(28)—F(4) | 104.4(7) |
| C(18)—N(2)—C(23) | 130.2(5) | F(3)—C(28)—C(30) | 112.9(8) |
| C(26)—N(6)—N(5) | 106.1(4) | F(4)—C(28)—C(30) | 107.6(7) |
| C(56)—O(6)—C(57) | 117.7(9) | F(3)—C(28)—C(29) | 111.6(5) |
| C(7)—C(6)—C(8) | 109.1(6) | F(4)—C(28)—C(29) | 104.4(7) |
| C(7)—C(6)—C(4) | 109.1(5) | C(30)—C(28)—C(29) | 114.9(7) |
| C(8)—C(6)—C(4) | 113.5(5) | O(3)—C(29)—N(7) | 126.0(6) |
| C(27)—N(5)—N(6) | 109.1(5) | O(3)—C(29)—C(28) | 117.1(5) |
| O(2)—C(5)—C(9) | 112.6(4) | N(7)—C(29)—C(28) | 116.8(5) |
| O(2)—C(5)—C(4) | 103.9(4) | N(7)—C(31)—C(33) | 111.3(5) |
| C(9)—C(5)—C(4) | 111.0(4) | N(7)—C(31)—C(32) | 106.7(4) |
| C(27)—N(4)—C(26) | 105.6(4) | C(33)—C(31)—C(32) | 116.8(4) |
| C(27)—N(4)—C(22) | 130.4(4) | O(4)—C(32)—C(36) | 112.0(4) |
| C(26)—N(4)—C(22) | 124.0(5) | O(4)—C(32)—C(31) | 106.9(4) |
| C(43)—O(4)—C(32) | 118.6(4) | C(36)—C(32)—C(31) | 109.4(4) |
| N(1)—C(4)—C(6) | 114.0(4) | C(34)—C(33)—C(31) | 109.6(5) |
| N(1)—C(4)—C(5) | 107.5(4) | C(34)—C(33)—C(35) | 111.1(6) |
| C(6)—C(4)—C(5) | 113.9(4) | C(31)—C(33)—C(35) | 113.2(5) |
| C(21)—N(3)—N(2) | 104.9(6) | C(37)—C(36)—C(41) | 120.0(5) |
| C(48)—N(8)—N(9) | 105.6(4) | C(37)—C(36)—C(32) | 119.6(5) |

TABLE 8-continued

| Bond angle (°) of compound of formula (I) | | | |
|---|---|---|---|
| | Bond angle/° | | Bond angle/° |
| O(10)—C(61)—C(62) | 90(2) | C(41)—C(36)—C(32) | 120.3(5) |
| O(7)—C(59)—O(10) | 108(2) | C(36)—C(37)—C(38) | 119.7(6) |
| O(7)—C(59)—C(60) | 131(2) | C(39)—C(38)—C(37) | 120.1(7) |
| O(10)—C(59)—C(60) | 108.4(12) | C(38)—C(39)—C(40) | 120.5(7) |
| C(29)—N(7)—C(31) | 122.8(5) | C(41)—C(40)—C(39) | 119.6(7) |
| C(10)—C(9)—C(14) | 119.2(5) | C(40)—C(41)—C(36) | 120.1(6) |
| C(10)—C(9)—C(5) | 121.9(5) | C(43)—C(42)—C(47) | 116.8(5) |
| C(14)—C(9)—C(5) | 118.9(5) | C(42)—C(43)—O(4) | 124.1(5) |
| N(8)—N(9)—C(46) | 110.1(4) | C(42)—C(43)—C(44) | 121.1(5) |
| N(8)—N(9)—C(50) | 118.8(4) | O(4)—C(43)—C(44) | 114.9(5) |
| C(46)—N(9)—C(50) | 131.1(5) | C(45)—C(44)—C(43) | 122.6(5) |
| C(12)—C(11)—C(10) | 120.4(6) | C(44)—C(45)—C(46) | 117.0(5) |
| C(54)—N(11)—N(12) | 108.0(5) | C(47)—C(46)—C(45) | 121.3(5) |
| C(9)—C(10)—C(11) | 120.5(5) | C(47)—C(46)—N(9) | 106.4(4) |
| C(59)—O(10)—C(61) | 105.0(15) | C(45)—C(46)—N(9) | 132.2(5) |
| C(54)—N(10)—C(49) | 132.6(5) | C(46)—C(47)—C(48) | 105.1(5) |
| C(54)—N(10)—C(53) | 105.1(5) | C(46)—C(47)—C(42) | 121.1(5) |
| C(49)—N(10)—C(53) | 122.3(5) | C(48)—C(47)—C(42) | 133.7(5) |
| C(53)—N(12)—N(11) | 107.6(5) | N(8)—C(48)—C(47) | 112.8(5) |
| C(11)—C(12)—C(13) | 120.1(6) | C(50)—C(49)—N(10) | 118.6(4) |
| C(14)—C(13)—C(12) | 119.2(6) | C(49)—C(50)—N(9) | 121.8(4) |
| C(13)—C(14)—C(9) | 120.7(6) | C(49)—C(50)—C(51) | 120.7(5) |
| C(20)—C(15)—O(2) | 123.8(5) | N(9)—C(50)—C(51) | 117.5(5) |
| C(20)—C(15)—C(16) | 122.1(5) | C(52)—C(51)—C(50) | 119.9(6) |
| O(2)—C(15)—C(16) | 114.1(5) | C(51)—C(52)—C(53) | 119.8(5) |
| C(17)—C(16)—C(15) | 121.6(5) | N(12)—C(53)—C(52) | 132.5(5) |
| C(19)—C(18)—N(2) | 106.8(5) | N(12)—C(53)—N(10) | 108.9(5) |
| C(19)—C(18)—C(17) | 121.5(5) | C(52)—C(53)—N(10) | 118.6(5) |
| N(2)—C(18)—C(17) | 131.6(5) | N(11)—C(54)—N(10) | 110.4(5) |
| C(16)—C(17)—C(18) | 116.7(5) | O(5)—C(56)—O(6) | 123.5(12) |
| C(18)—C(19)—C(20) | 121.5(6) | O(5)—C(56)—C(55) | 122.4(12) |
| C(18)—C(19)—C(21) | 104.5(5) | O(6)—C(56)—C(55) | 114.1(10) |
| C(20)—C(19)—C(21) | 134.0(6) | O(6)—C(57)—C(58) | 110.6(10) |

TABLE 9

| Torsion angle (°) of compound of formula (I) | | | |
|---|---|---|---|
| | Torsion angle/° | | Torsion angle/° |
| C(4)—N(1)—C(2)—O(1) | −7.2(9) | N(6)—N(5)—C(27)—N(4) | −0.3(7) |
| C(4)—N(1)—C(2)—C(1) | 168.4(5) | C(26)—N(4)—C(27)—N(5) | −0.1(7) |
| F(2)—C(1)—C(2)—O(1) | −161.6(6) | C(22)—N(4)—C(27)—N(5) | −177.0(6) |
| F(1)—C(1)—C(2)—O(1) | −44.6(7) | C(31)—N(7)—C(29)—O(3) | −1.9(11) |
| C(3)—C(1)—C(2)—O(1) | 75.8(8) | C(31)—N(7)—C(29)—C(28) | 175.6(6) |
| F(2)—C(1)—C(2)—N(1) | 22.5(7) | F(3)—C(28)—C(29)—O(3) | −170.8(8) |
| F(1)—C(1)—C(2)—N(1) | 139.4(5) | F(4)—C(28)—C(29)—O(3) | −58.6(9) |
| C(3)—C(1)—C(2)—N(1) | −100.2(7) | C(30)—C(28)—C(29)—O(3) | 59.0(10) |
| C(26)—N(6)—N(5)—C(27) | 0.5(7) | F(3)—C(28)—C(29)—N(7) | 11.5(11) |
| C(15)—O(2)—C(5)—C(9) | −70.4(6) | F(4)—C(28)—C(29)—N(7) | 123.7(7) |
| C(15)—O(2)—C(5)—C(4) | 169.4(4) | C(30)—C(28)—C(29)—N(7) | −118.7(8) |
| C(2)—N(1)—C(4)—C(6) | 110.0(6) | C(29)—N(7)—C(31)—C(33) | 108.3(6) |
| C(2)—N(1)—C(4)—C(5) | −122.8(5) | C(29)—N(7)—C(31)—C(32) | −123.2(6) |
| C(7)—C(6)—C(4)—N(1) | −75.5(6) | C(43)—O(4)—C(32)—C(36) | −70.8(6) |
| C(8)—C(6)—C(4)—N(1) | 46.5(7) | C(43)—O(4)—C(32)—C(31) | 169.5(4) |
| C(7)—C(6)—C(4)—C(5) | 160.7(5) | N(7)—C(31)—C(32)—O(4) | −170.7(4) |
| C(8)—C(6)—C(4)—C(5) | −77.4(6) | C(33)—C(31)—C(32)—O(4) | −45.6(6) |
| O(2)—C(5)—C(4)—N(1) | 176.9(4) | N(7)—C(31)—C(32)—C(36) | 67.8(5) |
| C(9)—C(5)—C(4)—N(1) | 55.6(5) | C(33)—C(31)—C(32)—C(36) | −167.0(5) |
| O(2)—C(5)—C(4)—C(6) | −55.8(5) | N(7)—C(31)—C(33)—C(34) | −59.1(7) |
| C(9)—C(5)—C(4)—C(6) | −177.1(4) | C(32)—C(31)—C(33)—C(34) | 178.0(6) |
| C(18)—N(2)—N(3)—C(21) | −0.6(10) | N(7)—C(31)—C(33)—C(35) | 65.5(7) |
| C(23)—N(2)—N(3)—C(21) | 176.2(7) | C(32)—C(31)—C(33)—C(35) | −57.3(7) |
| O(2)—C(5)—C(9)—C(10) | 138.6(5) | O(4)—C(32)—C(36)—C(37) | 148.2(5) |
| C(4)—C(5)—C(9)—C(10) | −105.3(6) | C(31)—C(32)—C(36)—C(37) | −93.6(6) |
| O(2)—C(5)—C(9)—C(14) | −42.2(7) | O(4)—C(32)—C(36)—C(41) | −35.6(7) |
| C(4)—C(5)—C(9)—C(14) | 73.8(6) | C(31)—C(32)—C(36)—C(41) | 82.7(6) |
| C(48)—N(8)—N(9)—C(46) | 1.4(7) | C(41)—C(36)—C(37)—C(38) | −1.5(9) |
| C(48)—N(8)—N(9)—C(50) | −177.7(5) | C(32)—C(36)—C(37)—C(38) | 174.7(6) |
| C(14)—C(9)—C(10)—C(11) | 0.7(9) | C(36)—C(37)—C(38)—C(39) | 1.3(10) |
| C(5)—C(9)—C(10)—C(11) | 179.8(5) | C(37)—C(38)—C(39)—C(40) | −0.1(11) |
| C(12)—C(11)—C(10)—C(9) | −1.0(10) | C(38)—C(39)—C(40)—C(41) | −0.9(12) |
| O(7)—C(59)—O(10)—C(61) | 40(2) | C(39)—C(40)—C(41)—C(36) | 0.7(11) |

TABLE 9-continued

| Torsion angle (°) of compound of formula (I) | | | |
|---|---|---|---|
| | Torsion angle/° | | Torsion angle/° |
| C(60)—C(59)—O(10)—C(61) | −173.9(10) | C(37)—C(36)—C(41)—C(40) | 0.6(9) |
| C(62)—C(61)—O(10)—C(59) | −174.6(10) | C(32)—C(36)—C(41)—C(40) | −175.7(6) |
| C(54)—N(11)—N(12)—C(53) | −0.1(8) | C(47)—C(42)—C(43)—O(4) | 178.5(5) |
| C(10)—C(11)—C(12)—C(13) | 0.4(11) | C(47)—C(42)—C(43)—C(44) | −1.6(8) |
| C(11)—C(12)—C(13)—C(14) | 0.5(12) | C(32)—O(4)—C(43)—C(42) | −1.1(8) |
| C(12)—C(13)—C(14)—C(9) | −0.9(12) | C(32)—O(4)—C(43)—C(44) | 179.0(5) |
| C(10)—C(9)—C(14)—C(13) | 0.3(10) | C(42)—C(43)—C(44)—C(45) | 3.9(8) |
| C(5)—C(9)—C(14)—C(13) | −178.8(7) | O(4)—C(43)—C(44)—C(45) | −176.2(5) |
| C(5)—O(2)—C(15)—C(20) | 0.9(8) | C(43)—C(44)—C(45)—C(46) | −2.6(8) |
| C(5)—O(2)—C(15)—C(16) | −179.9(4) | C(44)—C(45)—C(46)—C(47) | −0.8(8) |
| C(20)—C(15)—C(16)—C(17) | −2.5(9) | C(44)—C(45)—C(46)—N(9) | −177.8(6) |
| O(2)—C(15)—C(16)—C(17) | 178.3(5) | N(8)—N(9)—C(46)—C(47) | 0.3(6) |
| N(3)—N(2)—C(18)—C(19) | 1.4(8) | C(50)—N(9)—C(46)—C(47) | 179.2(6) |
| C(23)—N(2)—C(18)—C(19) | −174.9(7) | N(8)—N(9)—C(46)—C(45) | 177.6(6) |
| N(3)—N(2)—C(18)—C(17) | 177.5(7) | C(50)—N(9)—C(46)—C(45) | −3.4(10) |
| C(23)—N(2)—C(18)—C(17) | 1.1(12) | C(45)—C(46)—C(47)—C(48) | −179.4(6) |
| C(15)—C(16)—C(17)—C(18) | 2.6(8) | N(9)—C(46)—C(47)—C(48) | −1.7(6) |
| C(19)—C(18)—C(17)—C(16) | −1.7(9) | C(45)—C(46)—C(47)—C(42) | 3.0(9) |
| N(2)—C(18)—C(17)—C(16) | −177.3(6) | N(9)—C(46)—C(47)—C(42) | −179.3(5) |
| N(2)—C(18)—C(19)—C(20) | 177.2(7) | C(43)—C(42)—C(47)—C(46) | −1.7(8) |
| C(17)—C(18)—C(19)—C(20) | 0.7(11) | C(43)—C(42)—C(47)—C(48) | −178.5(7) |
| N(2)—C(18)—C(19)—C(21) | −1.6(8) | N(9)—N(8)—C(48)—C(47) | −2.6(8) |
| C(17)—C(18)—C(19)—C(21) | −178.1(7) | C(46)—C(47)—C(48)—N(8) | 2.8(8) |
| O(2)—C(15)—C(20)—C(19) | −179.5(6) | C(42)—C(47)—C(48)—N(8) | 180.0(7) |
| C(16)—C(15)—C(20)—C(19) | 1.3(10) | C(54)—N(10)—C(49)—C(50) | −175.8(6) |
| C(18)—C(19)—C(20)—C(15) | −0.4(10) | C(53)—N(10)—C(49)—C(50) | 1.5(8) |
| C(21)—C(19)—C(20)—C(15) | 178.0(9) | N(10)—C(49)—C(50)—N(9) | 177.0(5) |
| N(2)—N(3)—C(21)—C(19) | −0.4(11) | N(10)—C(49)—C(50)—C(51) | −3.4(8) |
| C(18)—C(19)—C(21)—N(3) | 1.3(11) | N(8)—N(9)—C(50)—C(49) | 148.8(6) |
| C(20)—C(19)—C(21)—N(3) | −177.3(9) | C(46)—N(9)—C(50)—C(49) | −30.1(9) |
| C(27)—N(4)—C(22)—C(23) | 179.2(6) | N(8)—N(9)—C(50)—C(51) | −30.8(8) |
| C(26)—N(4)—C(22)—C(23) | 2.8(9) | C(46)—N(9)—C(50)—C(51) | 150.3(6) |
| N(4)—C(22)—C(23)—N(2) | −177.2(6) | C(49)—C(50)—C(51)—C(52) | 2.9(10) |
| N(4)—C(22)—C(23)—C(24) | −1.7(11) | N(9)—C(50)—C(51)—C(52) | −177.5(6) |
| N(3)—N(2)—C(23)—C(22) | 138.0(8) | C(50)—C(51)—C(52)—C(53) | −0.4(10) |
| C(18)—N(2)—C(23)—C(22) | −45.8(11) | N(11)—N(12)—C(53)—C(52) | −178.6(7) |
| N(3)—N(2)—C(23)—C(24) | −37.6(11) | N(11)—N(12)—C(53)—N(10) | 0.1(7) |
| C(18)—N(2)—C(23)—C(24) | 138.6(8) | C(51)—C(52)—C(53)—N(12) | 177.2(7) |
| N(5)—N(6)—C(26)—N(4) | −0.5(6) | C(51)—C(52)—C(53)—N(10) | −1.4(10) |
| N(5)—N(6)—C(26)—C(25) | −179.4(7) | C(54)—N(10)—C(53)—N(12) | 0.0(7) |
| C(27)—N(4)—C(26)—N(6) | 0.4(7) | C(49)—N(10)—C(53)—N(12) | −178.0(5) |
| C(22)—N(4)—C(26)—N(6) | 177.5(5) | C(54)—N(10)—C(53)—C(52) | 178.9(6) |
| C(27)—N(4)—C(26)—C(25) | 179.4(6) | C(49)—N(10)—C(53)—C(52) | 0.9(8) |
| C(22)—N(4)—C(26)—C(25) | −3.4(9) | N(12)—N(11)—C(54)—N(10) | 0.1(8) |
| N(6)—C(26)—C(25)—C(24) | −178.3(8) | C(49)—N(10)—C(54)—N(11) | 177.7(6) |
| N(4)—C(26)—C(25)—C(24) | 2.9(11) | C(53)—N(10)—C(54)—N(11) | 0.0(7) |
| C(26)—C(25)—C(24)—C(23) | −1.9(14) | C(57)—O(6)—C(56)—O(5) | 10.5(17) |
| C(22)—C(23)—C(24)—C(25) | 1.4(14) | C(57)—O(6)—C(56)—C(55) | −168.3(12) |
| N(2)—C(23)—C(24)—C(25) | 177.0(8) | C(56)—O(6)—C(57)—C(58) | −170.7(9) |

Experimental Example 1: In Vitro Assay of Compounds for Repression of hMMP1 Transcriptional Activity in Luciferase Reporter Gene Screening System

Experimental Purpose

The human MMP-1 promoter region (containing two AP-1 binding sites and two PEA3 sites, a total of 249 bp, GenBank accession number of AF023338) was cloned upstream of the luciferase reporter gene. The hMMP-1 promoter reporter gene was constructed and transfected into Hela cells so that luciferase production could be readily detected. A stable recombinant hMMP-1/luciferase cell line was used for the development and validation of this experiment.

Culture Media and Reagents:

1. Conventional Cell Culture Medium

DMEM 90%, FBS 10%, 1 mM NEAA, 1 mM sodium pyruvate, 4 mM L-glutamine, 300 μg/mL G418, stored at 4° C.

2. Freezing Medium

DMEM 75%, FBS 20%, DMSO 5%. Prepared before use.

3. Experimental Cell Culture Medium

DMEM 97%, Charcoal stripped serum 3%.

4. Bright-Glo Kit

All of one vial of Bright Glo buffer was transferred to a brown fluorescent substrate vial, inverted and mixed until the substrate was completely dissolved, dispensed as needed, and stored at −80° C.

Method

Cell Suspension Preparation from Frozen Cells

1. Cell Thawing

1) Frozen cells were rapidly thawed by continuously stirring in a 37° C. water bath until completely dissolved.

2) The cells were added to a 10 mL centrifuge tube (containing 5 mL of pre-warmed cell culture medium), and then centrifuged at 1000 rpm for 5 minutes.

3) The supernatant was discarded, and the cells were resuspended in 10 mL of pre-warmed cell culture medium.

4) The cell suspension was transferred to a 100 mM cell culture dish and incubated in a 37° C., 5% $CO_2$ incubator.

2. Passaging

1) When cells were 80 to 90% confluent, cell passaging was performed. pGL6.0-TA-hMMP-1 HeLa cells were usually passaged twice a week at a dilution of 1:3 or 1:6.

2) All the culture medium was carefully aspirated, and the cell layer was gently rinsed with an appropriate amount of DPBS and aspirated.

3) The cells were added with an appropriate amount of 0.05% Typsine EDTA and incubated in a $CO_2$ incubator for 3 to 5 minutes to digest the cells.

4) The cells were resuspended in an appropriate amount of pre-warmed cell culture medium and diluted for passaging.

3. Changing the Culture Medium Every Other Day

1) All the culture medium was gently aspirated.

2) Fresh cell culture medium (pre-warmed at 37° C.) was added (an addition of 10 mL for a 100 mm dish).

4. Cell Freezing

1) Steps 1 to 4 of the passaging were repeated.

2) Cells were centrifuged at 1000 rpm for 5 minutes.

3) The supernatant was aspirated, and the cells were resuspended in freezing medium, counted, and diluted to a concentration of (2 to 3)$\times 10^6$ cells/mL. 1 mL of suspended cells were added to each cell cryogenic tube.

4) The cryogenic tubes were placed in a cryogenic box, which was then transferred to a −80° C. refrigerator overnight.

5) The cryogenic tubes were transferred to liquid nitrogen (−196° C.).

5. Cell Inoculation

1) All the culture medium was carefully aspirated, and the cell layer was gently rinsed with an appropriate amount of DPBS and aspirated.

2) The cells were added with an appropriate amount of 0.05% Typsine EDTA and incubated in a $CO_2$ incubator for 3 to 5 minutes to digest the cells.

3) The cells were resuspended in an appropriate amount of cell culture medium.

4) The number of cells required was calculated with a cell concentration of $5\times 10^3$ cells/well.

5) The cell suspension was diluted with an appropriate cell culture medium.

6) The cell suspension was dispensed into a sterile disposable reagent reservoir.

7) The cells were inoculated into a 384-well plate at 30 μL per well.

8) The cell plate was incubated in a 37° C., 5% $CO_2$ incubator for 18 to 24 hours.

Preparation of Compounds

1. PMA:

PMA was dissolved in DMSO and diluted to 1 mM, dispensed and stored in a −80° C. refrigerator away from light for later use.

2. Dexamethasone:

Dexamethasone was dissolved in DMSO and diluted to 30 mM, dispensed and stored in a −80° C. refrigerator away from light for later use.

3. Preparation of 10× Compound:

The test compound was diluted to 10 mM with DMSO, dispensed and stored in a −80° C. refrigerator for later use.

The compound was diluted to 1 mM, 0.25 mM, 0.0625 mM, 0.015625 mM, 0.0039 mM, 0.0009765 mM, 0.000244 mM, 0.000061 mM, 0.00001526 mM, and 0.0000038125 mM with DMSO, then diluted 100-fold with serum-free medium containing 100 nM PMA, and finally the 10× compound assay plate was obtained.

The final DMSO concentration was 0.1%. PMA needs to be protected from light during use.

hMMP1 GR Transcriptional Repression Activity Assay

1) Cell inoculation: Fresh cells were inoculated into a 384-well white assay plate at $5\times 10^3$ cells/30 μL/well and incubated in a 37° C., 5% $CO_2$ incubator for 24 hours.

2) Compound preparation: The compound plate was configured before the start of the experiment, then a 10-fold concentration of the reference compound (Dexamethasone) and the test compound were prepared, and finally a 10× compound assay plate was obtained.

3) Compound addition: 3.3 μL of 10× compound was transferred with Bravo and added to a cell plate. The cell plate was incubated in a 37° C., 5% $CO_2$ incubator for 18 hours.

4) 30 μL of Bright-Glo fluorescence assay reagent was transferred to the cell plate. 5) The cell plate was centrifuged and incubated for 2 minutes.

6) The fluorescence value was determined using an Envision plate reader.

Data Processing and Analysis

Positive control: 10 nM PMA+1000 nM Dexamethasone (0.1% DMSO)

Negative control: 10 nM PMA (0.1% DMSO)

Test compound: Maximum concentration 1000 nM, 4-fold dilution, 10 wells in total, repeated.

Dexamethasone: Maximum concentration 1000 nM, 4-fold dilution, 10 wells in total, repeated.

The concentration curve of the test compound was plotted using the graphing software GraphPad Prism5, and the $IC_{50}$ value was calculated.

The experimental results are shown in Table 10.

Experimental Example 2: In Vitro Assay of Compounds for Activation of MMTV Transcriptional Activity in Luciferase Reporter Gene Screening System Experimental Purpose:

The mouse mammary tumor virus (MMTV) promoter contains specific binding sites that activate GR (GREs). To determine the activity of the compound, a reporter gene (luciferase) was inserted behind the MMTV promoter, and the structure was expressed in a stable manner in the genome of the HeLa cell line. The MMTV promoter was activated using the test compound to induce the luciferase expression, and its activity was detected by luminescence measurements.

Culture Media and Reagents:

1. Conventional Cell Culture Medium

DMEM 90%, FBS 10%, Hygromycin 100 μg/mL.

2. Freezing Medium

DMEM 75%, FBS 20%, DMSO 5%.

3. Experimental Cell Culture Medium

DMEM 97%, Charcoal stripped serum 3%.

4. Bright-Glo Kit

All of one vial of Bright Glo buffer was transferred to a brown fluorescent substrate vial, inverted and mixed until the substrate was completely dissolved, dispensed as needed, and stored at −80° C.

Method

Cell Suspension Preparation from Frozen Cells

1. Cell Thawing

1) Frozen cells were continuously stirred in a 37° C. water bath until completely thawed.

2) The cells were added to a 15 mL centrifuge tube (containing 5 mL of pre-warmed cell culture medium), and then centrifuged at 1000 rpm for 5 minutes.

3) The supernatant was discarded, and the cells were resuspended in 5 mL of pre-warmed cell culture medium.

4) The cell suspension was transferred to a 60 mM cell culture dish and incubated in a 37° C., 5% $CO_2$ incubator.

2. Passaging

1) When cells were 80 to 90% confluent, cell passaging was performed. The cells were usually passaged twice a week at a dilution of 1:3 or 1:6.

2) All the culture medium was carefully aspirated, and the cell layer was gently rinsed with an appropriate amount of DPBS and aspirated.

3) The cells were added with an appropriate amount of 0.05% Typsine EDTA and incubated in a $CO_2$ incubator for 3 to 5 minutes to digest the cells.

4) The cells were resuspended in an appropriate amount of pre-warmed cell culture medium and diluted for passaging.

3. Changing the Culture Medium Every Other Day

1) All the culture medium was gently aspirated.

2) Fresh cell culture medium (pre-warmed at 37° C.) was added (an addition of 10 mL for a 100 mm dish).

4. Cell Freezing

1) Steps 1 to 4 of the passaging were repeated.

2) Cells were centrifuged at 1000 rpm for 5 minutes.

3) The supernatant was aspirated, and the cells were resuspended in freezing medium, counted, and diluted to a concentration of (2 to 3)$\times 10^6$ cells/mL. 1 mL of suspended cells were added to each cell cryogenic tube.

4) The cryogenic tubes were placed in a cryogenic box, which was then transferred to a −80° C. refrigerator overnight.

5) The cryogenic tubes were transferred to liquid nitrogen (−196° C.)

5. Cell Inoculation

1) All the culture medium was carefully aspirated, and the cell layer was gently rinsed with an appropriate amount of DPBS and aspirated.

2) The cells were added with an appropriate amount of 0.05% Typsine EDTA and incubated in a $CO_2$ incubator for 3 to 5 minutes to digest the cells.

3) The cells were resuspended in an appropriate amount of cell culture medium.

4) The number of cells required was calculated with a concentration of $4\times 10^3$ cells/well.

5) The cell suspension was diluted with an appropriate cell culture medium.

6) The cell suspension was dispensed into a sterile disposable reagent reservoir.

7) The cells were inoculated into a 384-well plate at 30 μL per well.

8) The cell plate was incubated in a 37° C., 5% $CO_2$ incubator for 18 to 24 hours.

Preparation of Compounds

1. Dexamethasone

Dexamethasone was dissolved in DMSO and diluted to 30 mM, dispensed and stored in a −80° C. refrigerator away from light for later use.

2. Preparation of 4× Compound:

The test compound was diluted to 10 mM with DMSO, dispensed and stored in a −80° C. refrigerator for later use.

The compound was diluted to 1 mM, 0.25 mM, 0.0625 mM, 0.015625 mM, 0.0039 mM, 0.0009765 mM, 0.000244 mM, 0.000061 mM, 0.00001526 mM, and 0.0000038125 mM with DMSO, then diluted 250-fold with culture medium containing Charcoal stripped serum, and finally the 4× compound assay plate was obtained and prepared before use.

The final DMSO experimental concentration was 0.1%.

MMTV_GR Transcriptional Activation Activity Assay

1) Cell inoculation: Fresh cells were inoculated into a 384-well white transparent bottom assay plate at $4\times 10^3$ cells/30 μL/well and incubated in a 37° C., 5% $CO_2$ incubator for 24 hours.

2) Compound preparation: The compound plate was configured before the start of the experiment. A 4-fold serial dilution of the reference compound (Dexamethasone) and the test compound were prepared, transferred to the assay plate with Echo at 100 nL per well, and then 25 μL of culture medium was added to each well, so that the plate was a 4× compound assay plate.

3) Compound addition: 10 μL of 4× compound was transferred from the compound assay plate with Bravo and added to a cell plate. The cell plate was incubated in a 37° C., 5% $CO_2$ incubator for 20 to 24 hours.

4) 30 μL of Bright-Glo fluorescence assay reagent was transferred to the cell plate.

5) The cell plate was centrifuged and incubated for 2 minutes.

6) The fluorescence value was determined using an Envision plate reader.

Data Processing and Analysis

Positive control: 1000 nM Dexamethasone (0.1% DMSO)

Negative control: 0.1% DMSO

Test compound: Maximum concentration 1000 nM, 4-fold dilution, 10 wells in total, repeated.

Dexamethasone: Maximum concentration 1000 nM, 4-fold dilution, 10 wells in total, repeated.

The concentration curve of the test compound was plotted using the graphing software GraphPad Prism5, and the $IC_{50}$ value was calculated.

The experimental results are shown in Table 10.

TABLE 10

In vitro screening test results of compound of the present disclosure

| | TR (hMMP1 transcriptional repression activity) | | TA (MMTV transcriptional activation activity) | |
|---|---|---|---|---|
| Test sample | $IC_{50}$ (nM) | Effect | $EC_{50}$ (nM) | Effect |
| Crystal form Q of compound of formula (I) | 2.25 | 84.79% | 7.72 | 63.86% |

Conclusion: The crystal form Q of the compound of formula (I) exhibits good transcriptional repression activity and considerable transcriptional activation activity.

Experimental Example 3: In Vivo PK Study of Crystal Form Q of Compound of Formula (I) in Lewis Female Rats 1 Research Methods and Experimental Design
1.1 Experimental System

TABLE 11

| Experimental system | |
|---|---|
| Species | Rat |
| Strain | Lewis |
| Source | Beijing Vital River Laboratory Animal Technology Co., Ltd. |
| Gender and number | 4 rats (female) |
| Weeks of age at the start of the experiment | 7 to 8 weeks old |
| Body weight at the start of the experiment | 120 to 160 g (female) |
| Rationality | Use as few animals as possible while meeting research objectives, scientific standards, and regulatory requirements. |

1.2 Environmental Adaptation/Inspection and Quarantine

Animals will undergo at least 3 days of adaptation after their arrival at the animal facility of WuXi AppTec. At the end of the adaptation period, a veterinarian or designated personnel will examine the health status of the animals to assess their suitability for the experimental research.

1.3 Animal Feeding

Animals in this experiment protocol will be housed in compliance with the U.S. Animal Welfare Act, the Guide for the Care and Use of Laboratory Animals (8th edition) by the National Research Council of the National Academy of Sciences, the Regulations for the Management of Laboratory Animals (revised edition in 2017), and other regulations and guiding principles. Animals will be housed in shared cages, but may be housed in individual cages after surgery, according to special experimental requirements, for behavioral or health reasons, or due to the death of a companion. Except for situations where fasting is required, qualified rat growth and reproduction feed is provided daily, and the animals have free access to food. Each batch of feed is provided with an analysis report on nutritional ingredients, chemical pollutants, and microorganisms, which is evaluated and approved by a veterinarian before being used on the animals. Drinking water for the animals is autoclaved reverse osmosis water supplied in drinking bottles, and the animals have free access to water. Drinking water is periodically tested by a qualified third-party testing laboratory for microorganisms and environmental pollutants, and the test report is reviewed and evaluated by the veterinarian. Animals are housed on wood shavings or corn cob bedding. If corn cob bedding is used, it will be replaced with wood shavings before fasting. Each batch of bedding is provided with an analysis report on environmental pollutants by the supplier, which is reviewed and approved by the veterinarian before use. Environmental conditions are controlled at a room temperature of 20° C. to 26° C., a relative humidity of 40% to 70%, and an alternating light-dark cycle of 12 hours. The light-dark cycle may be disturbed by experimental operations. The temperature and humidity are monitored in real-time by the Vaisala ViewLinc monitoring system.

1.4 Administration

On the day of the experiment, the animals in the first group were administered the crystal form Q of the compound of formula (I) at a concentration of 0.3 mg/mL in a single dose by gavage. The animals were weighed before administration, and the administration volume was calculated based on the body weight.

1.5 Dose Selection

Oral gavage (0.3 mg/kg).

1.6 Euthanasia

The animals used were euthanized by $CO_2$ anesthesia after the collection of PK samples at the last time point.

1.7 Animal Weight and Clinical Observations

On the day of administration, the appropriate animal weight was selected in strict accordance with the experimental protocol. The overall health status of the animals should be observed on the day of administration. The animals should be monitored at each sample collection time point or at each administration time point. Any anomalies during the experiment should be faithfully recorded.

2 Sample Collection 2.1 Drug Solution

After the preparation of each formulation, three samples of the gavage solution (a top layer, a middle layer, and a bottom layer) were collected for formulation analysis by HPLC-UV to examine the accuracy of the concentration of the formulation.

2.2 Sample Collection and Processing

Approximately 0.2 mL of whole blood sample was collected at the specified time by jugular venipuncture (or other appropriate blood collection site), and the actual blood collection time was recorded in the experimental record. The acceptable error for the collection time point is ±1 minute within 1 hour after administration, and ±5% of the theoretical time for other time points. All blood samples were immediately transferred to labeled commercial centrifuge tubes containing $K_2$-EDTA. After collection, the blood sample was centrifuged at 4° C., 3200 g for 10 minutes to aspirate the supernatant plasma, which was immediately placed in dry ice and then stored at −60° C. or lower for LC-MS/MS analysis.

3 Sample Analysis 3.1 Drug Solution

The concentration of the administered formulation was determined by HPLC-UV with the calibration curve containing at least 6 concentration levels. The actual measured concentration should be within 80 to 120% of the theoretical formulation concentration, otherwise the pharmacokinetic parameters should be calculated based on the actual dose.

3.2 Plasma Sample

The concentration of the test sample in plasma was determined by the LC-MS/MS bioanalytical method.

When analyzing samples by the LC-MS/MS bioanalytical method, at least one standard curve and two sets of quality control samples should be processed simultaneously in each run batch, and the number of quality control samples should be greater than 5% of the number of unknown samples. Calibration standards and quality control samples should be freshly prepared on the day of analysis.

The standard curve acceptance criteria for each analytical batch include: each standard curve contains 7 calibration standards at non-zero concentrations. The measured concentration of the calibration standards should be within ±20.0% of the indicated value, except for the lowest calibration standard, which should be within ±25.0%. At least 75% of the calibration standards in the standard curve should meet the acceptance criteria. If the calibration of the lower or upper limit of quantification of the standard curve does not meet the acceptance criteria, the limit of quantification will be increased or decreased accordingly.

The quality control sample acceptance criteria for each analytical batch include: each set of quality control samples contains at least 3 concentration levels (low, medium, and high), and the measured concentration of the quality control samples should be within ±20.0% of the indicated value. At least ⅔ of the quality control samples should meet the acceptance criteria.

Analyte interference: The mass spectral response of the analyte in both double blank and single blank samples should be less than 50% of the lower limit of quantification.

Residuals: System residuals are verified by injecting a blank sample immediately after the injection of the calibration standard at the highest concentration. The concentration of the analyte in residual samples is less than or equal to the lower limit of quantification (LLOQ) concentration.

The experimental results are shown in Table 12.

TABLE 12

In vivo pharmacokinetic experimental results of crystal form Q of compound of formula (I)

| Test sample | | Crystal form Q of compound of formula (I) |
|---|---|---|
| po (0.3 mg/kg) | Cmax (nmol/L) | 361 |
| | Tmax (h) | 4.5 |
| | AUC (h*nmol/L) | 3147 |
| | $T_{1/2}$ (h) | 3.57 |

Experimental conclusion: The crystal form Q of the compound of formula (I) has excellent pharmacokinetic properties.

What is claimed is:

1. A crystal form Q of a compound of formula (I), wherein the crystal form Q has an X-ray powder diffraction pattern comprising characteristic diffraction peaks at the following 2θ angles: 10.301±0.200°, 17.459±0.200°, and 19.141±0.200°, (I)

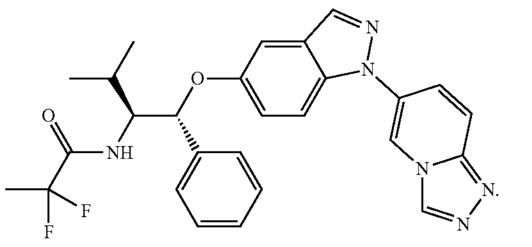

2. The crystal form Q according to claim 1, wherein the X-ray powder diffraction pattern of the crystal form Q comprises characteristic diffraction peaks at the following 2θ angles: 10.301±0.200°, 12.779±0.200°, 16.860±0.200°, 17.459±0.200°, 19.141±0.200°, 20.701±0.200°, 21.701±0.200°, and 24.400±0.200°.

3. The crystal form Q according to claim 2, wherein the X-ray powder diffraction pattern of the crystal form Q comprises characteristic diffraction peaks at the following 2θ angles: 8.060±0.200°, 10.301±0.200°, 12.779±0.200°, 16.860±0.200°, 17.459±0.200°, 17.870±0.200°, 18.639±0.200°, 19.141±0.200°, 20.701±0.200°, 21.701±0.200°, 22.579±0.200°, and 24.400±0.200°.

4. The crystal form Q according to claim 3, wherein the X-ray powder diffraction pattern of the crystal form Q comprises characteristic diffraction peaks at the following 2θ angles: 3.861±0.200°, 8.060±0.200°, 9.6210.200°, 10.301±0.200°, 11.500±0.200°, 12.779±0.200°, 16.860±0.200°, 17.459±0.200°, 17.870±0.200°, 18.639±0.200°, 19.141±0.200°, 20.701±0.200°, 21.701±0.200°, 22.579±0.200°, 24.400±0.200°, and 24.939±0.200°.

5. The crystal form Q according to claim 4, wherein the crystal form Q has an XRPD pattern as shown in FIG. 1.

6. The crystal form Q according to claim 2, wherein the crystal form Q has a differential scanning calorimetry curve comprising endothermic peaks with an onset at 181.4° C.±5° C.

7. The crystal form Q according to claim 6, wherein the crystal form Q has a DSC pattern as shown in FIG. 2.

8. The crystal form Q according to claim 2, wherein the crystal form Q has a thermogravimetric analysis curve with a weight loss of 1.47% at 150° C.±3° C.

9. The crystal form Q according to claim 8, wherein the crystal form Q has a TGA pattern as shown in FIG. 3.

10. A crystal form S of a compound of formula (I), wherein the crystal form S has an X-ray powder diffraction pattern comprising characteristic diffraction peaks at the following 2θ angles: 13.019±0.200°, 19.579±0.200°, and 20.262±0.200°, (I)

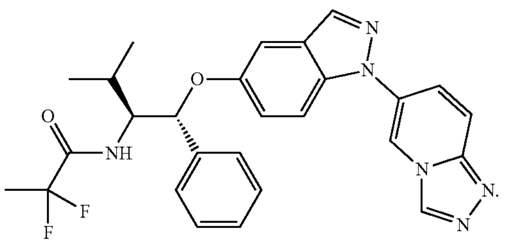

11. The crystal form S according to claim 10, wherein the X-ray powder diffraction pattern of the crystal form S comprises characteristic diffraction peaks at the following 2θ angles: 11.999±0.200°, 13.019±0.200°, 14.961±0.200°, 18.182±0.200°, 19.579-0.200°, 20.262±0.200°, 22.939±0.200°, and 24.021±0.200°.

12. The crystal form S according to claim 11, wherein the X-ray powder diffraction pattern of the crystal form S comprises characteristic diffraction peaks at the following 2θ angles: 3.201±0.200°, 11.463±0.200°, 11.999±0.200°, 13.019±0.200°, 14.523±0.200°, 14.961±0.200°, 18.182±0.200°, 19.579±0.200°, 20.262±0.200°, 22.939±0.200°, 24.021±0.200°, and 25.738±0.200°.

13. The crystal form S according to claim 12, wherein the crystal form S has an XRPD pattern as shown in FIG. 5.

14. The crystal form S according to claim 10, wherein the crystal form S has a differential scanning calorimetry curve comprising an endothermic peak at 114.9° C.±3° C.

15. The crystal form S according to claim 14, wherein the crystal form S has a DSC pattern as shown in FIG. 6.

16. The crystal form S according to claim 10, wherein the crystal form S has a thermogravimetric analysis curve with a weight loss of 0.99% at 90.0° C.±3° C. and a weight loss of 2.54% at 120.0° C.±3° C.

17. The crystal form S according to claim 16, wherein the crystal form S has a TGA pattern as shown in FIG. 7.

18. A method for treating rheumatoid arthritis in a subject in need thereof, comprising: administering the crystal form Q according to claim 1 to the subject.

19. A method for treating rheumatoid arthritis in a subject in need thereof, comprising: administering the crystal form S according to claim 10 to the subject.

* * * * *